US011813377B2

(12) United States Patent
Xie et al.

(10) Patent No.: US 11,813,377 B2
(45) Date of Patent: Nov. 14, 2023

(54) MICROFIBER STRUCTURES AND METHODS OF SYNTHESIS AND USE THEREOF

(71) Applicant: BOARD OF REGENTS OF THE UNIVERSITY OF NEBRASKA, Lincoln, NE (US)

(72) Inventors: Jingwei Xie, Omaha, NE (US); Jiang Jiang, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 17/317,234

(22) Filed: May 11, 2021

(65) Prior Publication Data
US 2021/0268154 A1   Sep. 2, 2021

Related U.S. Application Data

(63) Continuation of application No. 15/510,338, filed as application No. PCT/US2015/052858 on Sep. 29, 2015, now Pat. No. 11,033,659.

(60) Provisional application No. 62/056,899, filed on Sep. 29, 2014.

(51) Int. Cl.
| | |
|---|---|
| A61L 27/56 | (2006.01) |
| A61K 9/70 | (2006.01) |
| A61K 9/00 | (2006.01) |
| A61L 27/18 | (2006.01) |
| A61L 27/38 | (2006.01) |
| D01D 5/00 | (2006.01) |
| D01D 10/00 | (2006.01) |

(52) U.S. Cl.
CPC ............ *A61L 27/56* (2013.01); *A61K 9/0092* (2013.01); *A61K 9/70* (2013.01); *A61L 27/18* (2013.01); *A61L 27/38* (2013.01); *D01D 5/003* (2013.01); *D01D 10/00* (2013.01); *A61L 2400/12* (2013.01); *D10B 2331/041* (2013.01); *D10B 2401/10* (2013.01)

(58) Field of Classification Search
None
See application file for complete search history.

(56) References Cited

U.S. PATENT DOCUMENTS

| | | | |
|---|---|---|---|
| 3,674,540 A * | 7/1972 | Pergaminos | ............ B01J 20/22 8/138 |
| 6,653,005 B1 | 11/2003 | Muradov | |
| 7,704,740 B2 | 4/2010 | Schindler et al. | |

(Continued)

FOREIGN PATENT DOCUMENTS

| | | |
|---|---|---|
| CN | 102068716 A | 5/2011 |
| CN | 102071485 A | 5/2011 |

(Continued)

OTHER PUBLICATIONS

Gu, B.K., et al., "Fabrication of sonicated chitosan nanofiber mat with enlarged porosity for use as hemostatic materials" Carbohydr. Polym. (2013) 97(1):65-73.

(Continued)

*Primary Examiner* — Robert J Grun
(74) *Attorney, Agent, or Firm* — Robert C. Netter, Jr.; Dann, Dorfman, Herrell & Skillman

(57) ABSTRACT

Three dimensional nanofiber structures are provided and methods of production thereof.

14 Claims, 16 Drawing Sheets

(56) References Cited

U.S. PATENT DOCUMENTS

| | | | |
|---|---|---|---|
| 9,242,024 B2* | 1/2016 | Kwon | C08K 5/05 |
| 9,403,958 B2 | 8/2016 | Lindner et al. | |
| 9,655,995 B2 | 5/2017 | Xie | |
| 9,913,862 B2 | 3/2018 | Collins et al. | |
| 10,799,620 B2 | 10/2020 | Xie et al. | |
| 11,033,659 B2 | 6/2021 | Xie et al. | |
| 11,318,224 B2 | 5/2022 | Xie et al. | |
| 11,427,936 B2 | 8/2022 | Xie | |
| 2005/0084532 A1 | 4/2005 | Howdle et al. | |
| 2005/0187330 A1 | 8/2005 | Gulari et al. | |
| 2006/0002978 A1 | 1/2006 | Shea et al. | |
| 2007/0077272 A1 | 4/2007 | Li et al. | |
| 2008/0112998 A1 | 5/2008 | Wang | |
| 2010/0183699 A1 | 7/2010 | Wan et al. | |
| 2011/0070151 A1 | 3/2011 | Braithwaite et al. | |
| 2011/0195123 A1 | 8/2011 | Shemi | |
| 2011/0293685 A1 | 12/2011 | Kuo et al. | |
| 2012/0040581 A1 | 2/2012 | Kim | |
| 2012/0226295 A1 | 9/2012 | Jabbari | |
| 2013/0095167 A1 | 4/2013 | Warnke | |
| 2013/0112625 A1 | 5/2013 | Bahukudumbi et al. | |
| 2014/0024760 A1 | 1/2014 | Kwon et al. | |
| 2014/0051169 A1 | 2/2014 | Ganey et al. | |
| 2016/0015792 A1 | 1/2016 | Hendricus van Pinxteren et al. | |
| 2016/0015952 A1 | 1/2016 | Omachi et al. | |
| 2016/0106548 A1 | 4/2016 | Li et al. | |
| 2016/0176714 A1 | 6/2016 | Do et al. | |
| 2017/0296703 A1 | 10/2017 | Xie et al. | |
| 2019/0209732 A1 | 7/2019 | Xie et al. | |
| 2020/0164107 A1 | 5/2020 | Xie et al. | |
| 2020/0277711 A1 | 9/2020 | Xie | |
| 2021/0268154 A1 | 9/2021 | Xie et al. | |

FOREIGN PATENT DOCUMENTS

| | | |
|---|---|---|
| CN | 102703996 A | 10/2012 |
| CN | 103382625 A | 11/2013 |
| CN | 104464712 A | 3/2015 |
| CN | 105012991 B | 1/2018 |
| EP | 1611877 A1 | 1/2006 |
| EP | 2813212 A1 | 12/2014 |
| JP | 2006-169497 A | 6/2006 |
| JP | 2007160691 A | 6/2007 |
| JP | 2007222477 A | 9/2007 |
| JP | 4656320 B2 | 3/2011 |
| KR | 101493444 B1 | 2/2015 |
| WO | 00/50104 A1 | 8/2000 |
| WO | 2006/019600 A2 | 2/2006 |
| WO | 2009/011658 A1 | 1/2009 |
| WO | 2009/088777 A1 | 7/2009 |
| WO | 2014/037651 A1 | 3/2014 |
| WO | 2014/191739 A1 | 12/2014 |
| WO | 2015/051042 A2 | 4/2015 |

OTHER PUBLICATIONS

Nazarov, R., et al., "Porous 3-D scaffolds from regenerated silk fibroin" Biomacromolecules (2004) 5(3):718-26.

Joshi, M.K., et al., "Multi-layered macroporous three-dimensional nanofibrous scaffold via a novel gas foaming technique" Chem. Engr. J. (2015) 275:79-88.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension By a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

Ma, B., et al., "Rational design of nanofiber scaffolds for orthopedic tissue repair and regeneration" Nanomedicine (2013) 8(9):1459-81.

Dehghani, et al., "Engineering porous scaffolds using gas-based techniques" Current Opinion in Biotechnology (2011) 22:661-666.

Mulmi, et al., "Fabrication of Air Freshening Spongy Three Dimensional Electrospun Membrane" Journal of the Institute of Engineering (2018) 14(1):14-21.

Keit, et al., "Expansion of Two-dimension Electrospun Nanofiber Mats into Three-dimension Scaffolds" J. Vis. Exp. (2018):e58918.

Liu, Y., et al., "Composite vascular scaffold combining electrospun fibers and physically-crosslinked hydrogel with copper wire-induced grooves structure" J. Meeh. Behav. Biomed. Mater. (2016) 61:12-25.

Zhao, Y., et al., "Preparation of Nanofibers with Renewable Polymers and Their Application in Wound Dressing" Intl. J. Polmer Sci. (2016) 2016:4672839.

Pok, S., et al., "A multilayered scaffold of a chitosan and gelatin hydrogel supported by a PCL core for cardiac tissue engineering" Acta Biomater. (2013) 9(3):5630-5642.

Xie, J, et al., "Controlled biomineralization of electrospun poly(ϵ-caprolactone) fibers for enhancing their mechanical properties" Acta Biomaterialia (2013) 9(3):5698-5707.

Xie, J., et al., "The differentiation of embryonic stem cells seeded on electrospun nanofibers into neural lineages" Biomaterials (2009) 30(3):354-362.

Chen, S., et al.,. "Recent advances in electrospun nanofibers for wound healing" Nanomedicine (Lond.) (2017) 12 (11):1335-1352.

Electrospin Tech, "Post-electrospinning expansion of 2D membrane to 3D scaffold using gas foaming" (Oct. 27, 2015) available at: http://electrospintech.com/gasfoam3d.html#.X5bnPC9h0kg.

Borjigin, M., et al., "Proliferation of Genetically Modified Human Cells on Electrospun Nanofiber Scaffolds" Mol. Ther.-Nuc. Acids (2012) 1:e59.

Geiger, B.C., et al., "Dual drug release from CO2-infused nanofibers via hydrophobic and hydropjilic interactions" J. Appl. Polym. Sci. (2015) 132:42571.

Ayodeji, O., et al., "Carbon dioxide impregnation of electrospun polycaprolactone fibers" J. Supercritical Fluids (2007) 41:173-178.

Lee, S.J., et al., "The use of thermal treatments to enhance the mechanical properties of electrospun poly(E-caprolactone) scaffolds" Biomaterials (2008) 29:1422-1430.

Xie, J., et al., "Electrospray in the dripping mode for cell microencapsulation" J. Colloid Interface Sci. (2007) 312:247-255.

Cai, H., et al., "Aerogel Microspheres from Natural Cellulose Nanofibrils and Their Application as Cell Culture Scaffold" Biomacromolecules (2014) 15:2540-2547.

Liu, Y., et al., "HB-EGF embedded in PGA/PLLA scaffolds via subcritical CO2 augments the production of tissue engineered intestine" Biomaterials (2016) 103:150-159.

Wei, et al., "The multifunctional wound dressing with core-shell structured fibers prepared by coaxial electrospinning" Front. Mater. Sci. (2016) 10(2): 113-121.

Kang, et al., "Chitosan-coated poly(vinyl alcohol) nanofibers for wound dressings" J. Biomed. Mater. Res. B Appl. Biomater. (2010) 92(2):568-76.

* cited by examiner

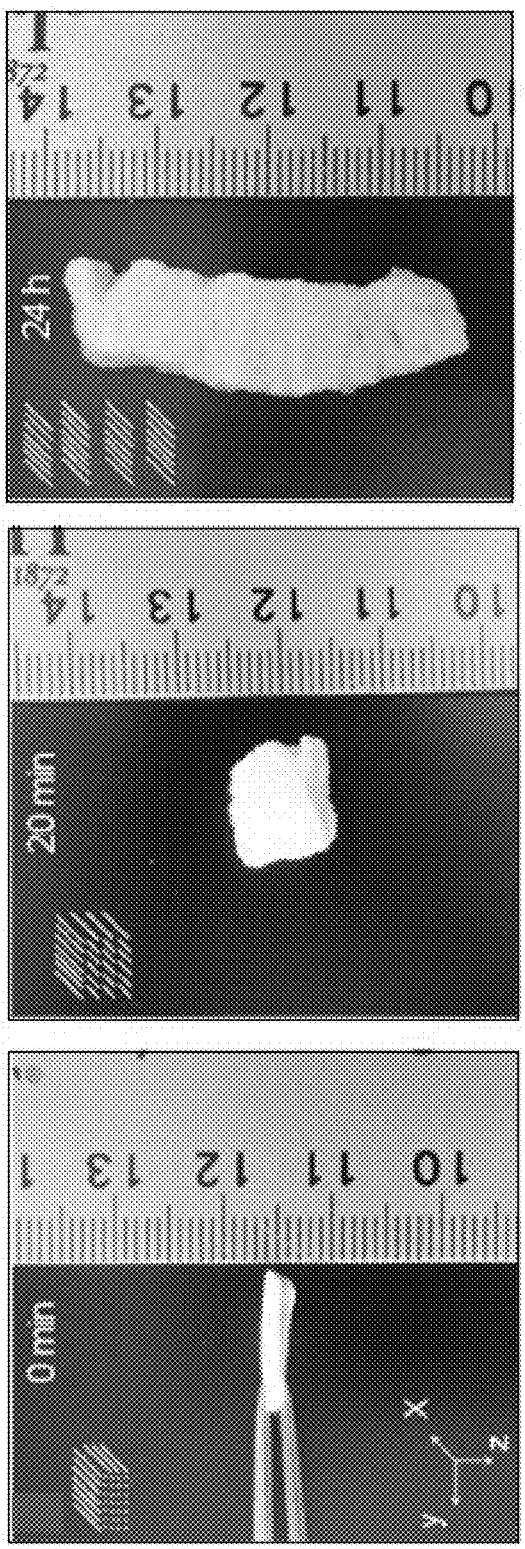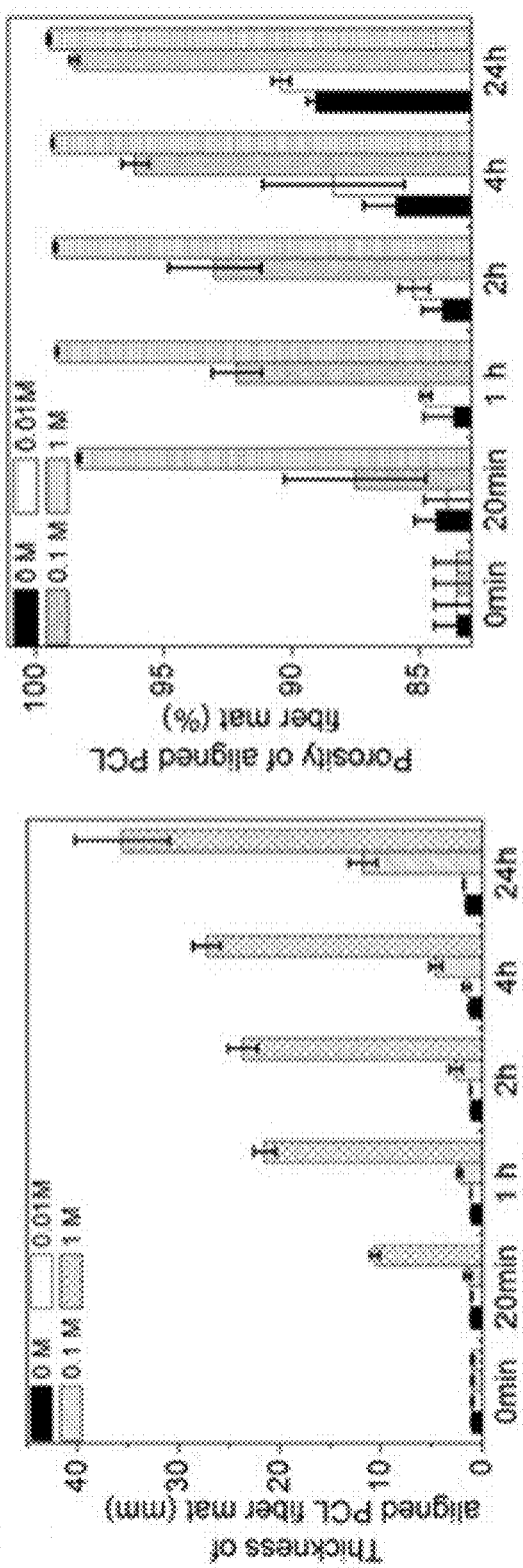
Figure 1A
Figure 1B
Figure 1C

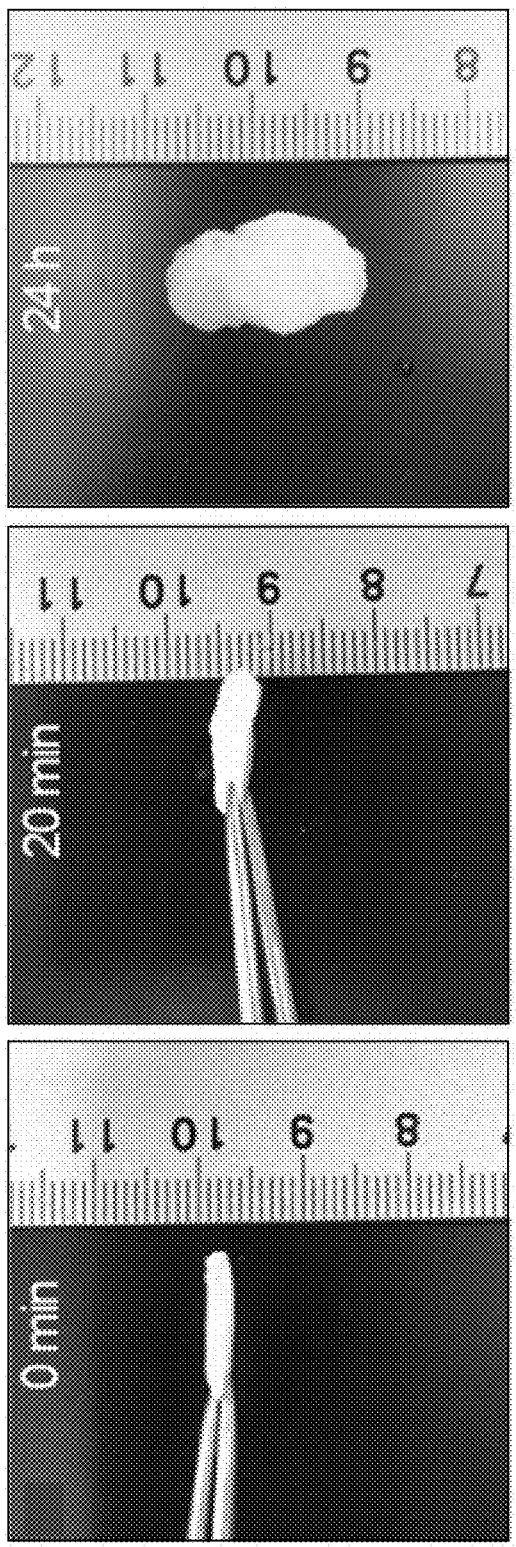
Figure 3A
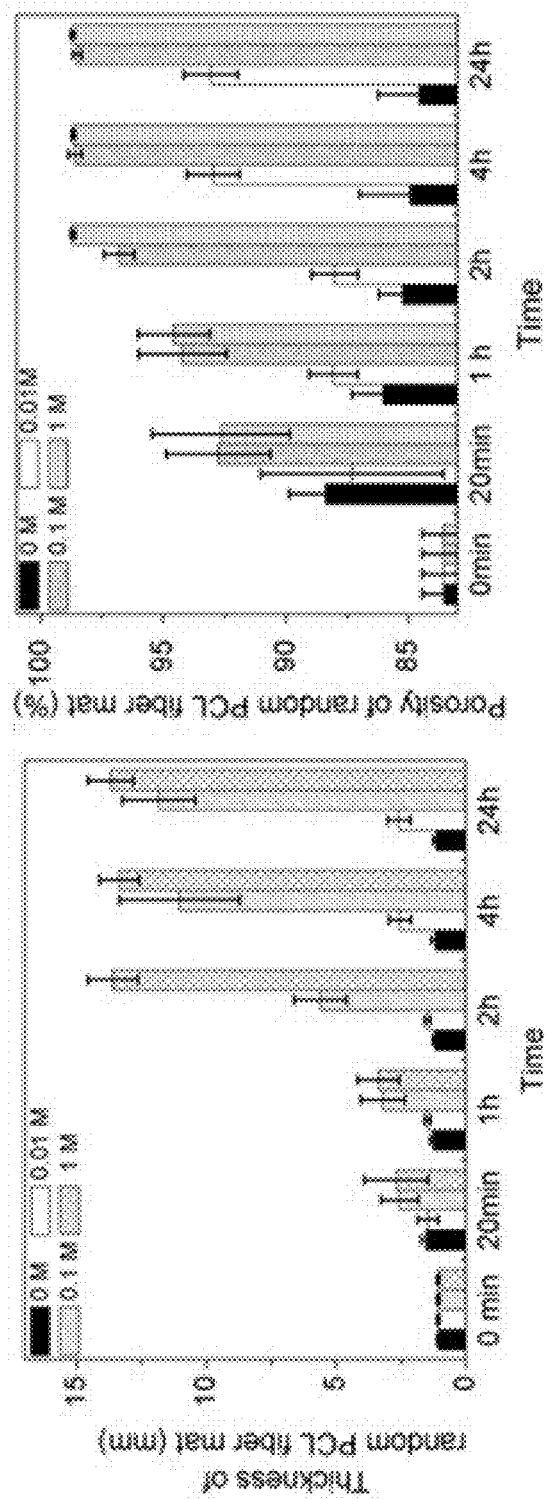
Figure 3B
Figure 3C

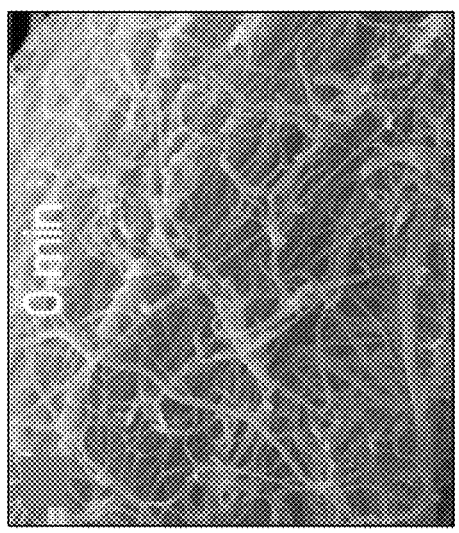
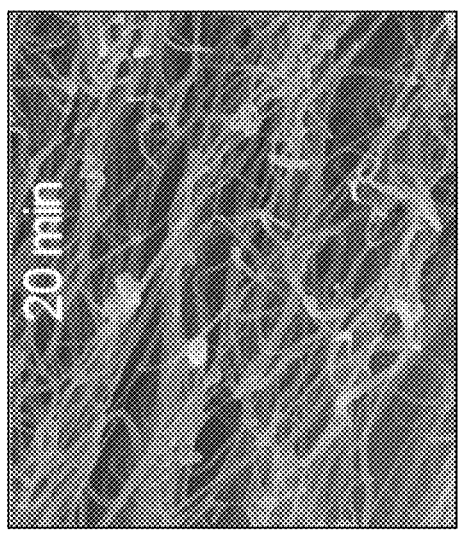
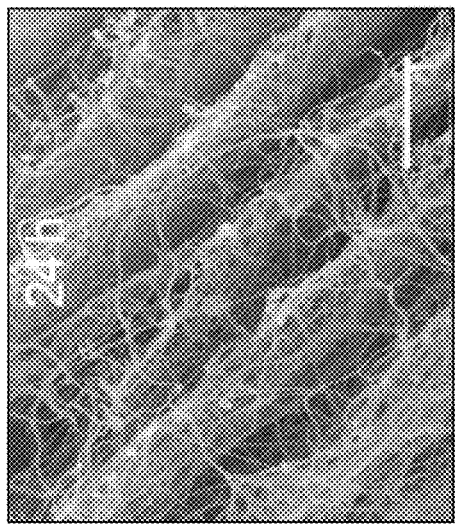
Figure 3D
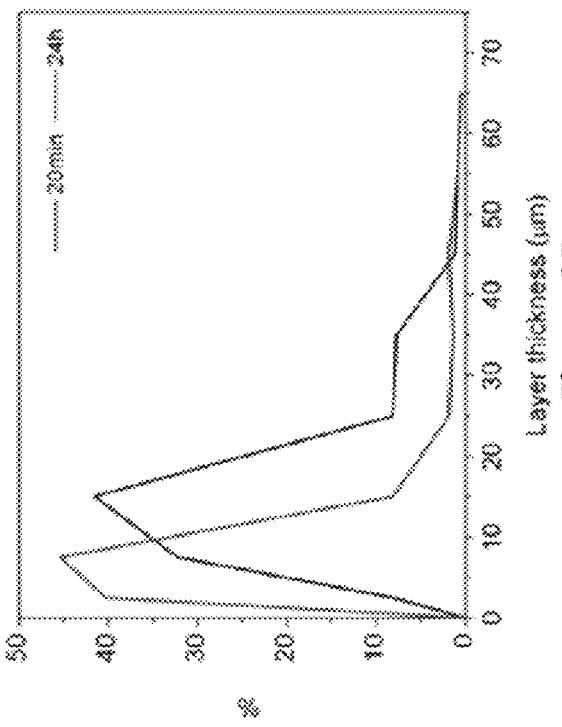
Figure 3F
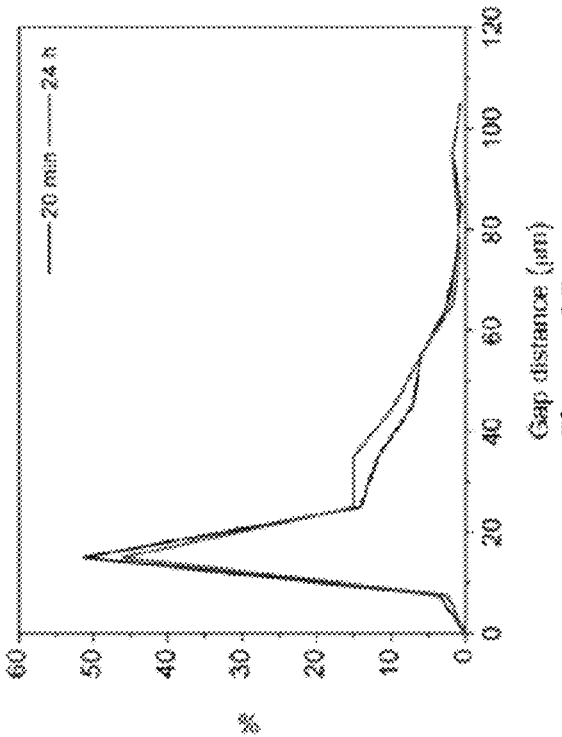
Figure 3E

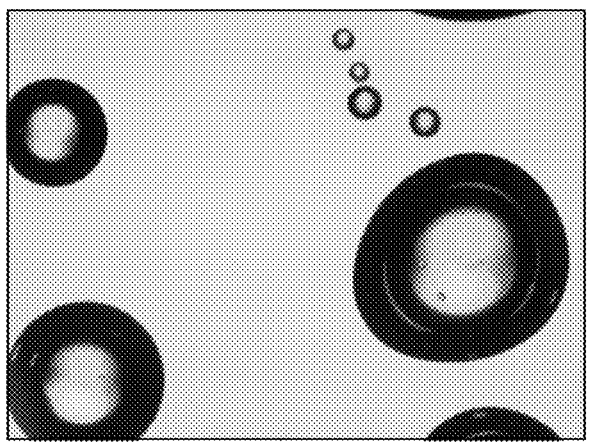
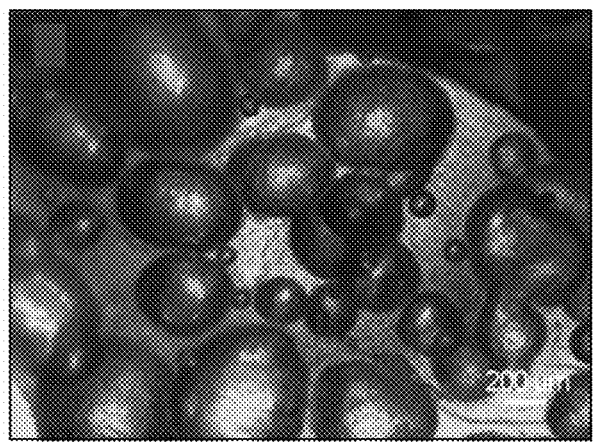
Figure 8A                              Figure 8B

MICROFIBER STRUCTURES AND METHODS OF SYNTHESIS AND USE THEREOF

This application is a continuation of U.S. patent application Ser. No. 15/510,338, filed Mar. 10, 2017, which is a § 371 application of PCT/US2015/052858, filed Sep. 29, 2015, which claims priority under 35 U.S.C. § 119(e) to U.S. Provisional Patent Application No. 62/056,899, filed Sep. 29, 2014. The foregoing applications are incorporated by reference herein.

This invention was made with government support under Grant No. 2P20 GM103480 awarded by the National Institutes of Health. The government has certain rights in the invention.

FIELD OF THE INVENTION

This application relates to the fields of nanofibers and nanofiber structures. More specifically, this invention provides methods for increasing the thickness and/or porosity of nanofiber structures.

BACKGROUND OF THE INVENTION

Several publications and patent documents are cited throughout the specification in order to describe the state of the art to which this invention pertains. Each of these citations is incorporated herein by reference as though set forth in full.

Regenerative medicine is a multidisciplinary subject that contains three major elements: cells, scaffolds, and signaling molecules (Khademhosseini et al. (2006) Proc. Natl. Acad. Sci., 103:2480-2487). Scaffolds play an important role as they not only provide a substrate for cellular adhesion and proliferation but can also deliver various cues to regulate cellular response for tissue regeneration (Grafahrend et al. (2011) Nat. Mater., 10:67-73). Multiple microfabrication techniques have been developed for the fabrication of scaffolds (Derby, B. (2012) Science 338:921-926; Moutos et al. (2007) Nat. Mater., 6:162-167; Wegst et al. (2015) Nat. Mater., 14:23-36). Electrospun nanofibers have shown great promise as a scaffold for regenerative medicine because of their biomimicry of the architecture of extracellular matrix (ECM) and the size of ECM collagen fibrils (Xie et al. (2008) Macromol. Rapid Commun., 29:1775-1792; Liu et al. (2012) Adv. Healthcare Mater., 1:10-25). Traditional electrospinning typically produces uncontrolled and densely packed fibers, however, resulting incompact two-dimensional (2D) nanofiber mats/membranes and hindrance of both cell infiltration and growth throughout the nanofiber scaffolds. Thus, traditional 2D nanofiber mats are limited as an ideal substrate for their applications in regenerative medicine and engineered three-dimensional (3D) tissue models (Bhardwaj et al. (2010) Biotechnol. Adv., 28:325-347).

To overcome this great obstacle, a number of attempts have been made to develop 3D electrospun nanofiber scaffolds capable of enhancing cellular ingrowth (Blakeney et al. (2011) Biomaterials, 32:1583-1590; Lee et al. (2011) Tissue Eng., Part A, 17:2695-2702; Cai et al. (2013) Langmuir 29:2311-2318; Sheikh et al. (2014) Nanomedicine 11:681-691; Jeong et al. (2014) J. Mater. Chem. B, 2:8116-8122). Unfortunately, most approaches have been restricted to the fabrication of 3D nanofiber scaffolds composed of randomly oriented nanofibers and/or certain materials (e.g., with additives) (Jin et al. (2015) Angew. Chem., Int. Ed., 54:7587-7591). These approaches often led to insufficient thickness and/or restricted geometry and/or uncontrolled porosity. In addition, previous 3D scaffolds obtained were associated with unordered structures and lack of nanotopographic cues that are critical for regeneration of organized tissues such as tendon, nerve, and muscle (Liu et al. (2012) Adv. Healthcare Mater., 1:10-25; Ma et al. (2013) Nanomedicine 8:1459-1481). Alternatively, other studies have been devoted to the use of electrospun fibers with much larger diameters (≈several to tens of µm) in order to enhance cellular infiltration (Fong et al. (2013) Proc. Natl. Acad. Sci., 110:6500-6505; Soliman et al. (2011) J. Biomed. Mater. Res., Part A, 96A:566-574). Such microfibers lack the biomimetic properties and nanotopographic cues, resulting in different cellular responses compared to the use of nanofibers. For a notable example, nanofiber scaffolds can minimize the inflammatory response when compared with films and microfiber scaffolds (Saino et al. (2011) Biomacromolecules 12:1900-1911). Furthermore, infiltrated cells are still predominantly distributed in the superficial part of microfiber scaffolds (Fong et al. (2013) Proc. Natl. Acad. Sci., 110: 6500-6505). It is desirable to preserve the specific nanotopographical cues such as anisotropic properties rendered by aligned nanofibers for 3D electrospun scaffolds. Such nanotopographical cues can be used as regulators of cellular behaviors (e.g., promotion of cytoskeletal reorganization and cellular and nuclear elongation of human mesenchymal stem cells, guidance, and enhancement of human dermal fibroblast migration and axonal outgrowth, and regulation of tendon stem cell differentiation) for favorite tissue regeneration (Dang et al. (2007) Adv. Mater., 19:2775-2779; Patel et al. (2007) Nano Lett., 7:2122-2128; Yin et al. (2010) Biomaterials 31:2163-2175). It is therefore imperative to develop a simple, controllable, and effective method for generating 3D electrospun nanofiber scaffolds capable of supporting cellular infiltration and organization with highly ordered structure and uniform cellular distribution after cell seeding and proliferation.

SUMMARY OF THE INVENTION

In accordance with the present invention, methods for producing a nanofibrous structure with increased porosity and/or thickness are provided. The method comprises exposing a nanofiber structure (e.g., mat) comprising a plurality of nanofibers to gas bubbles. The gas bubbles may be generated by a chemical reaction and/or physical means. In a particular embodiment, the gas bubbles are generated as a product of a chemical reaction (e.g., the hydrolysis of sodium borohydride). The method may also comprise preparing the nanofiber structure comprising a plurality of nanofibers (e.g., uniaxially-aligned, random, entangled, and/or electrospun fibers) prior to exposure to the gas bubbles. The method may further comprise washing the nanofibrous structure after exposure to the gas bubbles, removing gas bubbles trapped within the nanofibrous structure, and/or lyophilizing the produced nanofibrous structure.

In accordance with another aspect of the instant invention, three-dimensional nanofibrous structures having increased thickness and/or porosity are provided.

BRIEF DESCRIPTION OF THE DRAWINGS

FIGS. 1A, 1B, and 1C show the expansion and characterization of aligned nanofiber scaffolds. FIG. 1A: Photographs of aligned PCL fiber mats which were treated with 1 M NaBH$_4$ for 0 minutes, 20 minutes, and 24 hours. Inset shows a corresponding schematic. FIG. 1B: Thickness of aligned PCL fiber mats were measured after immersing in water, 0.01 M, 0.1 M, 1 M $NaBH_4$ for 20 minutes, 1 hour, 2 hours, 4 hours, and 24 hours. FIG. 1C: Corresponding porosities of aligned PCL fiber mats were estimated after immersing in water, 0.01 M, 0.1 M, 1 M $NaBH_4$ for 20 minutes, 1 hour, 2 hours, 4 hours, and 24 hours.

FIG. 2A: SEM images showing cross section morphologies of aligned PCL fiber mats before and after expansion in 1 M $NaBH_4$ solution for 20 minutes and 24 hours. The scale bar is 20 µm. FIG. 2B: Distributions of gap distances between adjacent layers of nanofiber scaffolds after expanding for 20 minutes and 24 hours. FIG. 2C: Distributions of layer thicknesses of nanofiber scaffolds after expanding for 20 minutes and 24 hours. Both gap distance and layer thickness were measured based on SEM images by the ImageJ software.

FIGS. 3A, 3B, 3C, 3D, 3E, and 3F show the expansion and characterization of random nanofiber scaffolds. FIG. 3A: Photographs showing random PCL nanofiber mats pre- and post-treatment with the 1 M aqueous solution of $NaBH_4$ for 20 minutes and 24 hours. FIG. 3B: SEM images showing cross-section morphologies of PCL nanofiber mats pre- and post-treatment with the 1 M aqueous solution of $NaBH_4$ for 20 minutes and 24 hours. FIG. 3C: Thickness of random nanofiber mats pre- and post-treatment with the 1 M aqueous solution of $NaBH_4$ for different times. FIG. 3D: Porosities of random nanofiber mats were estimated pre- and post-treatment with the 1 M aqueous solution of $NaBH_4$ for different times. The scar bar is 20 µm. FIG. 3E: Distributions of gap distances between adjacent layers of random nanofiber scaffolds after expanding for 20 minutes and 24 hours. FIG. 3F: Distributions of layer thicknesses of random nanofiber scaffolds after expanding for 20 minutes and 24 hours. Both gap distance and layer thickness were measured based on SEM images by the ImageJ software.

FIG. 4A: Photographs showing tubular scaffolds made of random nanofibers in the outer layer and longitudinally aligned nanofibers in the inner layer (RLA) before and after treatment with 1 M $NaBH_4$ for 1 and 24 hours. FIG. 4B: Photographs showing tubular scaffolds made of random nanofibers in the outer layer and circumferentially aligned nanofibers in the inner layer (RCA) before and after treatment with 1 M $NaBH_4$ for 1 and 24 hours. FIG. 4C: Change of inner and outer diameters of tubular scaffolds (RLA) after treatment with 1 M $NaBH_4$ solution for different times. FIG. 4D: Change of inner and outer diameters of tubular scaffolds (RCA) before and after treatment with 1 M $NaBH_4$ solution for different times.

FIGS. 8A and 8B show gas bubble formation. Optical microscopy images show gas bubble formation in the $NaBH_4$ solution in the absence (FIG. 8A) and presence (FIG. 8B) of electrospun nanofiber scaffolds.

DETAILED DESCRIPTION OF THE INVENTION

Figure 2A:
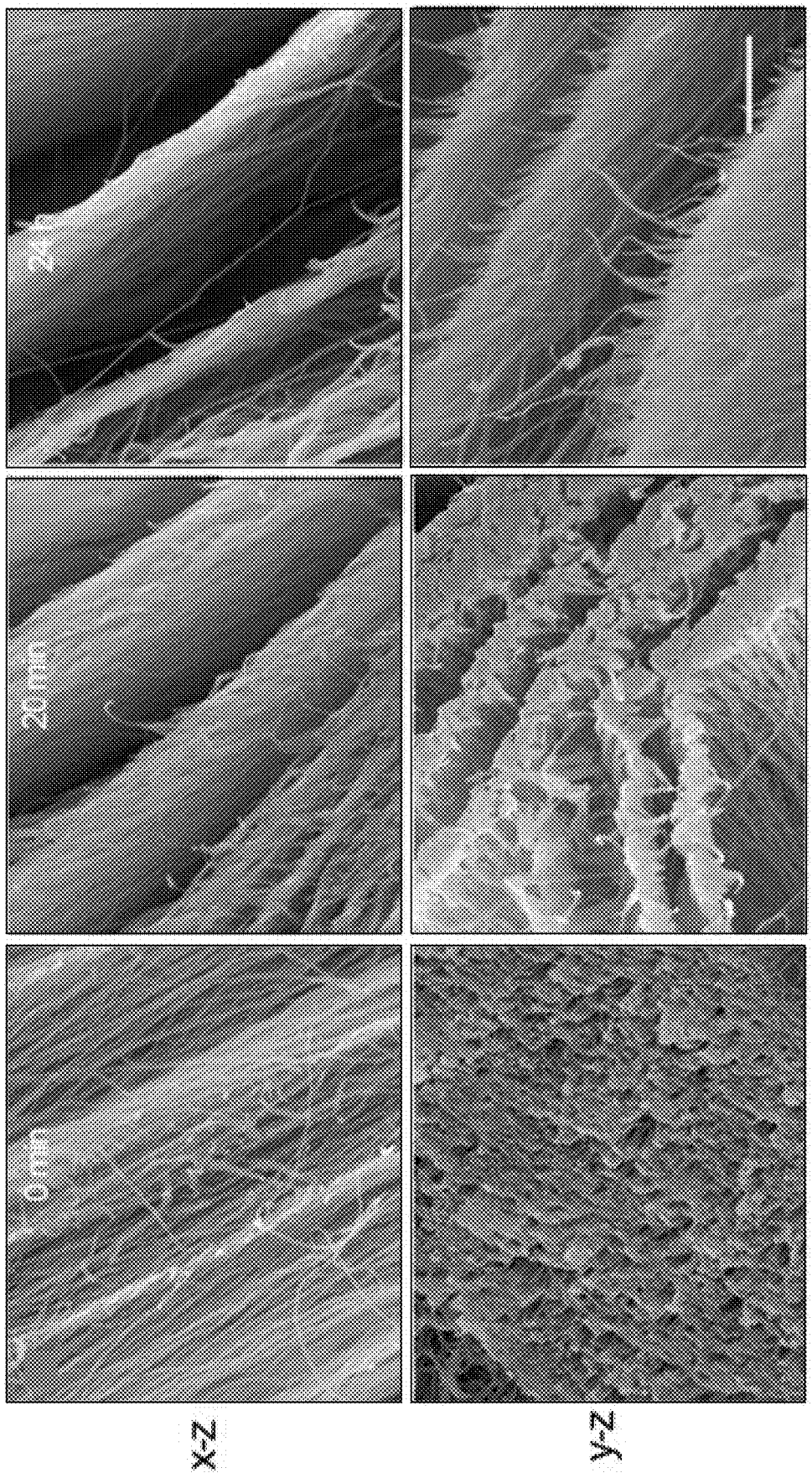
FIGS. 2A, 2B, and 2C show the morphology and microstructure of aligned nanofiber scaffolds.

Electrospun nanofibers have shown great potential as scaffolds for regenerative medicine because of its biomimicry. However, traditional two-dimensional electrospun nanofiber mats inhibit their applications because of the dense structure and lack of effective cell infiltration as well as a lack of oxygen and nutrient diffusion. Herein, a new method of expanding electrospun nanofiber mats in the third dimension, particularly using a modified gas-foaming technique, is provided. The resulting nanofiber scaffolds show layered structures with controllable gap widths and layer thicknesses on the order of microns. Expanded nanofiber scaffolds possess significantly higher porosity than traditional two-dimensional nanofiber membranes, while simultaneously maintaining nanotopographic cues. The distributions of gap widths and layer thicknesses are directly dependent on the processing time of nanofiber mats within the gas bubble forming solution. In vitro testing demonstrates robust cellular infiltration and proliferation within expanded nanofiber scaffolds as compared to limited cellular proliferation on the surface of traditional nanofiber mats. Importantly, cell alignment was observed throughout the expanded and aligned nanofiber scaffolds after incubation for 7 days. The presented method was further applied to fabricate tubular scaffolds composed of expanded nanofibers. Together, this novel class of scaffolds holds significant promise for applications in regenerative medicine and building 3D in vitro tissue models for drug screening and biological study.

Previous methods used to increase the porosity of the nanofiber scaffolds mainly include ultrasonication, increasing fiber diameter, and selective removal of sacrificial fiber (Lee et al. (2011) Tissue Eng. Part A., 17:2695-702; Pham et al. (2006) Biomacromolecules 7:2796-805; Baer et al. (2008) Biomaterials 29:2348-58; Kidoaki et al. (2005) Biomaterials 26:37-46; Yang et al. (2009) Tissue Eng. A., 15:945-56; Zhou et al. (2006) Polymer 47:7497-505; Brown et al. (2011) Adv. Mater., 23:5651-7; Bkakeney et al. (2011) Biomaterials 32(6):1583-90; Zhang et al. (2007) Adv. Mater., 19:3664-7; Xie et al. (2011) Small 7:293-7; Thandayamoorthy et al. (2006) J. Appl. Polym. Sci., 101:3121-4; Yan et al. (2011) Langmuir 27:4285-9; Xie et al. (2012) Adv. Healthcare Mater., 1:674-8; Lee et al. (2010) Tissue Eng. C. Methods 17:651-61). These technologies, however, are still associated with limited porosity, inefficiencies in production, complex methods, time consuming processes, and a requirement for special costly equipment. Advantages of the instant invention include, without limitation: 1) the range of porosity is larger than currently available technologies; 2) there is no requirement of special equipment after regular fiber fabrication; 3) it is suitable for most polymer fibers; (4) the technology can be easily extended to fabricate other medical devices for regeneration of nerve and intestine tissues and blood vessels, and (5) the process is simple and easy to be industrialized.

The gas foaming technique usually involves three basic steps: (1) polymer/gas solution formation, (2) gas bubble (pore) nucleation, and (3) gas bubble (pore) growth and volume expansion (Park et al. (1995) Polym. Eng. Sci., 35:432-440). Gas bubbles/foaming processes have many applications in the fields of material science (e.g., manufacturing foams and hollow metallic spheres), environmental management (e.g., water treatment), medicine (e.g., medical imaging, therapeutics, and carriers for gas, drug, and gene), and the food industry (e.g., food mixing and enhancement of texture) (Rodriguez-Rodriguez et al. (2015) Annu. Rev. Fluid Mech., 47:405-429; Lindner et al. (2004) Nat. Rev. Drug Discovery 3:527-533; Lee et al. (2015) Soft Matter 11:2067-2079; Sirsi et al. (2009) Bubble Sci., Eng., Technol., 1:3-17). Although gas foaming can be used to fabricate sponge scaffolds with high porosities for applications in tissue engineering, it has not been used to inflate electrospun nanofiber mats (Nam et al. (2000) J. Biomed. Mater. Res., 53:1-7).

The present invention relates to new microfiber (>1 μm diameter) and nanofiber (<1 μm diameter) structures (e.g., mats) and methods to expand the third dimension of microfiber or nanofiber structures (e.g., mats) in a post process manner to increase the porosity of the structures. While the application generally describes the modification of nanofiber structures and the synthesis of three-dimensional nanofibrous structures, the instant invention also encompasses the modification of microfiber structures and the synthesis of three-dimensional microfibrous structures. The methods may utilize chemical reactions and/or physical means to generate gas bubble formation. The fibers of the instant invention can be fabricated by any method and then may be placed into conditions (e.g., submerged or immersed in a liquid) wherein gas bubbles are generated for various amounts of time.

Electrospun nanofibers are usually deposited on a substrate to form a nanofiber mat. However, the fiber mats are often dense and hard to achieve suitable porosity for cell infiltration due to its intrinsic drawbacks. This invention provides a simple method to expand the third dimension of nanofiber mats by making use of bubbles (e.g., generated by chemical reactions in an aqueous solution). For example, the bubbles may be generated, without limitation, using a gas-production chemical reactions; by dissolved gas in a liquid under a high pressure and/or a low temperature; pressurized gas (e.g., $CO_2$) liquid; and/or physical means (e.g., laser (e.g., pulsed laser), acoustic induced, or flow induced). The methods of the instant invention may also be used to enlarge the porosity of other types of fibrous materials (i.e., not limited to electrospun nanofibers). The obtained scaffolds can mimic the architecture of extracellular matrix. The obtained scaffolds may also have large porosities, thereby allowing cells to infiltrate easily. The nanofiber scaffold generated by the methods of the instant invention can be used for tissue regeneration (e.g. bone, tendon, cartilage, skin, nerve, and/or blood vessel). Combining with cells, three dimensional tissue constructs can be readily formed to repair damaged tissues or organs.

A salt leaching/gas foaming method has been utilized for generation of dual-porosity nanofiber scaffolds (Lee et al. (2005) Biomaterials 26:3165-3172). Ammonium bicarbonate was used as a gas foaming agent. However, this method was associated with the use of relatively high temperature (90° C.) for leaching out the $NH_4HCO_3$ particles and generating gaseous ammonia and carbon dioxide within the solidified polymer matrix. In addition, layered structures and maintenance of nanotopographical cues were not presented. Another study only examined random fiber membranes using a gas foaming technique (Joshi et al. (2015) Chem. Eng. J., 275:79-88).

Herein, a new method is provided for three-dimensionally expanding nanofiber mats (e.g., electrospun nanofiber mats; e.g., mats comprising poly(ε-caprolactone) (PCL, an FDA-approved, biocompatible, and biodegradable polymer)) utilizing a modified gas foaming technique, optionally, followed by freeze-drying. The ability of this process to reliably generate 3D nanofiber scaffolds with a highly ordered architecture, ideal for supporting and organizing infiltrating and proliferating cells, is demonstrated.

In accordance with the instant invention, methods for producing a three-dimensional nanofibrous (or microfibrous) structure are provided. In other words, the method increases the thickness and/or porosity of a nanofibrous (or microfibrous) structure (e.g., comprising a plurality of nanofibers (or microfibers) (e.g., uniaxially-aligned, random, entangled, and/or electrospun)). The method comprises exposing a nanofibrous (or microfibrous) structure (e.g., a mat) to gas bubbles. As explained herein, the bubbles can be generated by chemical reactions or physical manipulations. For example, the nanofibrous structure can be submerged or immersed in a bubble/gas producing chemical reaction or physical manipulation. Generally, the longer the exposure to the bubbles, the greater the thickness and porosity of the nanofibrous structure increases. The nanofibrous structure may also be expanded within a mold (e.g., a metal, plastic, or other material that does not expand in the presence of gas bubbles) such that the expanded nanofibrous structure forms a desired shape (e.g., a tube). The nanofibrous structure may be treated with air plasma prior to exposure to gas bubbles (e.g., to increase hydrophilicity).

After exposure to the bubbles, the nanofibrous structure may be washed or rinsed in water and/or a desired carrier or buffer (e.g., a pharmaceutically or biologically acceptable carrier). Trapped gas bubbles may be removed by applying a vacuum to the nanofibrous structure. For example, the expanded nanofibrous structure may be submerged or immersed in a liquid (e.g., water and/or a desired carrier or buffer) and a vacuum may be applied to rapidly remove the gas bubbles. After expansion (e.g., after rinsing and removal of trapped gas), the nanofibrous structures may be lyophilized and/or freeze-dried.

The methods of the instant invention may further comprise synthesizing the nanofibrous structure (e.g., mat) prior to exposure to the gas bubbles. In a particular embodiment, the nanofibrous structure is synthesized using electrospinning. In a particular embodiment, the nanofibrous structure comprises uniaxially aligned fibers, random fibers, and/or entangled fibers. The nanofibrous structure may be cut or shaped prior to expansion.

The gas bubbles of the instant invention can be made by any method known in the art. The bubbles may be generated, for example, by chemical reactions or by physical approaches. In a particular embodiment, the chemical reaction or physical manipulation does not damage or alter or does not substantially damage or alter the nanofibers (e.g., the nanofibers are inert within the chemical reaction and not chemically modified). As explained hereinabove, the nanofibrous structure may be submerged or immersed in a liquid comprising the reagents of the bubble-generating chemical reaction. Examples of chemical reactions that generate bubbles include, without limitation:

$$NaBH_4 + 2H_2O = NaBO_2 + 4H_2$$

$$NaBH_4 + 4H_2O = 4H_2(g) + H_3BO_3 + NaOH$$

$$HCO_3^- + H^+ = CO_2 + H_2O$$

$$NH_4^+ + NO_2^- = N_2 + 2H_2O$$

$$H_2CO_3 = H_2O + CO_2$$

$$2H^+ + S^{2-} = H_2S$$

$$2H_2O_2 = O_2 + 2H_2O$$

$$3HNO_2 = 2NO + HNO_3 + H_2O$$

$$HO_2CCH_2COCH_2CO_2H = 2CO_2 + CH_3COCH_3$$

$$2H_2O_2 = 2H_2 + O_2$$

$$CaC_2 + H_2O = C_2H_2$$

$$Zn + 2HCl = H_2 + ZnCl_2$$

$$2KMnO_4 + 16HCl = 2KCl + 2MnCl_2 + H_2O + 5Cl_2$$

In a particular embodiment, the chemical reaction is the hydrolysis of $NaBH_4$ (e.g., $NaBH_4 + 2H_2O = NaBO_2 + 4H_2$). In a particular embodiment, $CO_2$ gas bubbles (generated chemically or physically (see below)) are used for hydrophilic polymers.

Examples of physical approaches for generating bubbles of the instant invention include, without limitation: 1) create high pressure (fill gas)/heat in a sealed chamber and suddenly reduce pressure; 2) dissolve gas in liquid/water in high pressure and reduce pressure to release gas bubbles; 3) use supercritical fluids (reduce pressure) like supercritical $CO_2$; 4) use gas liquid (then reduce pressure) (e.g., liquid $CO_2$, liquid propane and isobutane); 5) fluid flow; 6) apply acoustic energy or ultrasound to liquid/water; 7) apply a laser (e.g., to a liquid or water); 8) boiling; 9) reduce pressure boiling (e.g., with ethanol); and 10) apply radiation (e.g., ionizing radiation on liquid or water). The nanofibrous structure may be submerged or immersed in a liquid of the bubble-generating physical manipulation.

The nanofibers of the instant invention may comprise any polymer. In a particular embodiment, the polymer is biocompatible and/or biodegradable. The polymer may by hydrophobic, hydrophilic, or amphiphilic. In a particular embodiment, the polymer is hydrophobic. The polymer may be, for example, a homopolymer, random copolymer, blended polymer, copolymer, or a block copolymer. Block copolymers are most simply defined as conjugates of at least two different polymer segments. The polymer may be, for example, linear, star-like, graft, branched, dendrimer based, or hyper-branched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: polyvinyl alcohol (PVA), poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(2-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO. Amphiphilic copolymers may comprise a hydrophilic polymer (e.g., segment) and a hydrophobic polymer (e.g., segment) from those listed above (e.g., gelatin/PVA, PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA).

In accordance with the instant invention, three-dimensional nanofibrous structures are provided. In a particular embodiment, the nanofibrous structures are produced by the methods of the instant invention. The nanofibrous structures may be contained within water or a biologically and/or pharmaceutically acceptable carrier. The nanofibrous structure may be a scaffold for biomedical research such as regenerative medicine or tissue model. Applications for nanofibrous structures are provided in Xie et al. (Macromol. Rapid Commun. (2008) 29:1775-1792; incorporated by reference herein). In a particular embodiment, the nanofibrous structure comprises or encapsulates at least one agent (e.g., a therapeutic agent, growth factor, signaling molecule, cytokine, antibiotic, etc.). In a particular embodiment, the nanofibers of the instant invention (in the methods of synthesis or the final product) are labeled or modified with at least one agent or compound (e.g., a therapeutic agent, a therapeutic agent, growth factor, signaling molecule, cytokine, antibiotic, etc.), using either surface conjugation/coating and/or encapsulation (e.g., to modulate cellular responses and/or encourage tissue regeneration).

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The following examples are provided to illustrate certain embodiments of the invention. They are not intended to limit the invention in any way.

Example I

Materials and Methods

Fabrication of Electrospun Nanofiber Scaffolds

Nanofibers were produced utilizing a standard electrospinning setup following established protocols (Xie et al. (2009) Biomaterials 30:354-362; Xie et al. (2013) Acta Biomater., 9:5698-5707; Jiang et al. (2015) Pharm. Res., 32:2851-2862). PCL (Mw=80 kDa) was dissolved in a solvent mixture consisting of dichloromethane (DCM) and N,N-dimethylformamide (DMF) with a ratio of 4:1 (v/v) at a concentration of 10% (w/v). PCL solutions were pumped at a flow rate of 0.8 mL/hour using a syringe pump while an electrical potential of 15 kV was applied between the spinneret (a 22-gage needle) and a grounded collector located 20 cm apart from the spinneret. Aligned and random nanofiber mats 1 mm thick were collected on a drum rotating at speeds of 2000 and 100 rpm, respectively. Nanofiber mats were cut in liquid nitrogen to avoid deformation on the edge. Tubular nanofiber scaffolds were fabricated by depositing a 1 mm thick layer of aligned nanofibers followed by a 50 µm thick layer of random nanofibers. To fabricate tubular scaffolds made of random nanofibers in the outer layer and longitudinally aligned nanofibers, the obtained fiber mats were manually rolled over in two different directions (parallel and vertical) and sealed the edges with a 30% PCL DCM solution to form dual-layered tubular nanofiber scaffolds composed of random nanofibers in the outer layer and longitudinally or circumferentially aligned nanofibers in the inner layer. To generate gas bubbles in the solution, the following chemical reaction was chosen for a "proof-of-concept":

$$NaBH_4 + 2H_2O \rightarrow NaBO_2 + 4H_2\uparrow$$

NaBH$_4$ has been extensively investigated for H$_2$ storage and generation because of its relatively high hydrogen content (10.9%) and a controllable hydrolysis reaction (Ye et al. (2007) J. Power Sources 164:544-548; Liu et al. (2009) J. Power Sources 187:527-534). PCL nanofiber mats (1 cm×1 cm×1 mm) were employed to investigate the effects of the expansion process. PCL nanofiber mats were immersed in 40 mL fresh prepared NaBH$_4$ solutions and shaken at 50 rpm for varying lengths of time (0 minutes, 20 minutes, 1, 2, 4, and 24 hours) at 21° C. NaBH$_4$ solutions were prepared at 0.01, 0.1, and 1 M. Sample thickness was measured at 0 minutes, 20 minutes, 1 hour, 2 hours, 4 hours, and 24 hours using a vernier caliper while sample morphology was documented via a digital camera. Following expansion, the NaBH$_4$ solution was discarded and the expanded PCL nanofiber scaffolds were gently transferred into a beaker and rinsed three times with deionized water. To remove trapped gas bubbles, the expanded scaffolds were immersed in water and exposed to a vacuum (~200 Pa) for 3 seconds. Finally, expanded nanofiber scaffolds were rinsed additional three times with deionized water.

Characterization of Nanofiber Scaffolds

Tubular nanofiber scaffolds were made of random fibers in the outer layer and aligned fibers in the inner layer as mentioned above. Tubular scaffolds were expanded in the 1 M NaBH$_4$ solution similar to planar nanofiber mats. The inner and outer diameters of the tubular scaffolds were measured using a vernier caliper and digital photographs were taken at 0 minutes, 20 minutes, 1 hour, 2 hours, 4 hours, and 24 hours. SEM was used to examine fiber architectures upon cross sections of tubular scaffolds before and after the expansion procedure. The mean thickness of nanofiber mats and diameter of tubular scaffolds were reported across at least three independent experiments. The porosity of nanofiber scaffolds was calculated according to the volume change of nanofiber scaffolds pre- and post-expansion. Porosity was calculated using the following equation $$\varepsilon = [(V-V_0)/V]100\%$$

where $\varepsilon$ is porosity, V=L (length)×W (width)×T (thickness) is the volume of PCL nanofiber scaffold, $V_0=((m_0)/(\rho_0))$ is the calculated volume of bulk PCL material, $m_0$ is the mass of bulk PCL material, and $\rho_0$ is the density of bulk PCL materials.

PCL nanofiber mats were embedded in deionized water and frozen at −20° C. pre- and post-expansion. Cross sections of frozen nanofiber scaffolds were obtained using a cryostat and freeze-dried. SEM (FEI, Quanta 200, Oregon) was used to characterize nanofiber morphologies and architecture within cross sections of scaffolds. To avoid charging, nanofiber samples were fixed on a metallic stud with double-sided conductive tape and sputter-coated with platinum for 4 minutes under vacuum at a current intensity of 10 mA. SEM images were acquired at an accelerating voltage of 30 kV. Gap distances and layer thicknesses observed in nanofiber scaffolds pre- and post-expansion using 1 M NaBH$_4$ for 20 minutes and 24 hours were measured based on SEM images by the ImageJ software. At least 250 gaps or layers have been analyzed.

Mechanical properties of nanofiber scaffolds pre-expansion (1 cm×1 cm×1 mm) and post-expansion (1 cm×1 cm×1 cm) were measured. Nanofiber samples were mounted between two steel grips and two 1.5 cm diameter glass coverslips in order to measure tensile and compressive modulus, respectively. After equilibration, the trigger for tensile and compressive test and rate was set at 750 μN and 5.0×10$^{-3}$ s$^{-1}$. The resulting force (F) and length changing (ΔL) were recorded by the loading cell and digital data acquisition system. Engineering stress ($\sigma$=F/A) and engineering strain ($\varepsilon$=ΔL/L$_0$) were calculated by dividing the resulting force (F) and length changing (ΔL) over the cross-sectional area (A) and initial length (L$_0$). Young's modulus was given by E=$\sigma$/$\varepsilon$. Testing ceased when the maximum force reached 500 mN or the samples broke. Testing of aligned PCL nanofiber scaffolds post-expansion, including maximum stress, ultimate tensile stress, and ultimate tensile strain, was completed parallel to the axis of fiber alignment (y axis) and orthogonal to the axis of fiber alignment (z axis). Testing of random PCL nanofiber scaffolds post-expansion, including the maximum stress, ultimate tensile stress, and ultimate tensile strain, was completed orthogonally to the axis of fiber alignment (z axis). Mechanical testing was performed on at least five independent samples per material/condition.

In Vitro Cell Culture

Expanded PCL nanofiber scaffolds (1 cm×5 mm×1 cm) and unexpanded nanofiber mats (1 cm×5 mm×1 mm) were sterilized in 70% ethanol overnight and rinsed 3 times with PBS. Prior to cell culture, samples were immersed in media for 24 hours. Unexpanded and expanded nanofiber scaffolds were then placed in 24-well plates. 1×10$^6$ NIH3T3 cells were seeded on each nanofiber sample and incubated for 3 hours. Samples were then turned over and an equivalent number of cells were seeded on the alternate side and incubated for 3 hours. Samples were then transferred from 24-well plates to conical test tubes containing 25 mL of complete DMEM culture medium.

Histology Staining

Cultures were harvested at 1 day or 7 days after cell seeding. Both PCL nanofiber mats and expanded scaffolds were rinsed three times with PBS and fixed in 4% paraformaldehyde for 30 minutes at room temperature. All the samples were embedded within the freezing medium. A cryostat was employed to cut and the sections of 20 μm thick, which were collected at every 1 mm throughout the frozen block. Sections were baked at 50° C. overnight. Hematoxylin and eosin (H&E) staining was applied for distinguishing cells from nanofiber scaffolds following the manufacture's instructions, wherein cell nuclei stained blue and the cytoplasm and ECM stained pink (Fischer et al. (2008) Cold Spring Harb Protoc., pdb.prot4986). Briefly, sections were hydrated in distilled water prior to applications of Hematoxylin Mayer's solution for 5 minutes. Slides were thoroughly rinsed with distilled water. Adequate Bluing Reagent was applied to completely cover the sections and incubated for 10-15 seconds. Slides were rinsed 2 times with distilled water and then dipped in absolute alcohol. Adequate Eosin Y solution was then applied and incubated for 2-3 minutes. Slides were then rinsed using absolute alcohol and dehydrated with absolute alcohol. Slides were then mounted in the synthetic resin. In vitro experimental data was obtained from three independent experiments. Images were captured by a Ventana's Coreo Au slide scanner. Three sections were evaluated for each nanofiber material and processing condition.

Results

Electrospun nanofiber mats were successfully expanded in the third dimension after treatment with the NaBH$_4$ aqueous solutions (FIG. 1A). The terminal thickness of treated nanofiber mats increased with increasing time in solution and with increasing concentration of NaBH$_4$ (FIG. 1B). Surprisingly, the thickness of nanofiber mats increased from 1 mm to 35.6 mm after only 24 hour treatment with the 1 M NaBH$_4$ aqueous solution. Similarly, the porosity of aligned PCL nanofiber scaffolds increased with increasing the reaction time and increasing concentration of NaBH$_4$, which was in line with the trend of thickness (FIG. 1C). The scaffold porosity increased to 99.2% after treatment with a 1 M NaBH$_4$ aqueous solution for 24 hours from a baseline porosity of 83.6% for the starting nanofiber mat.

Figure 2C:
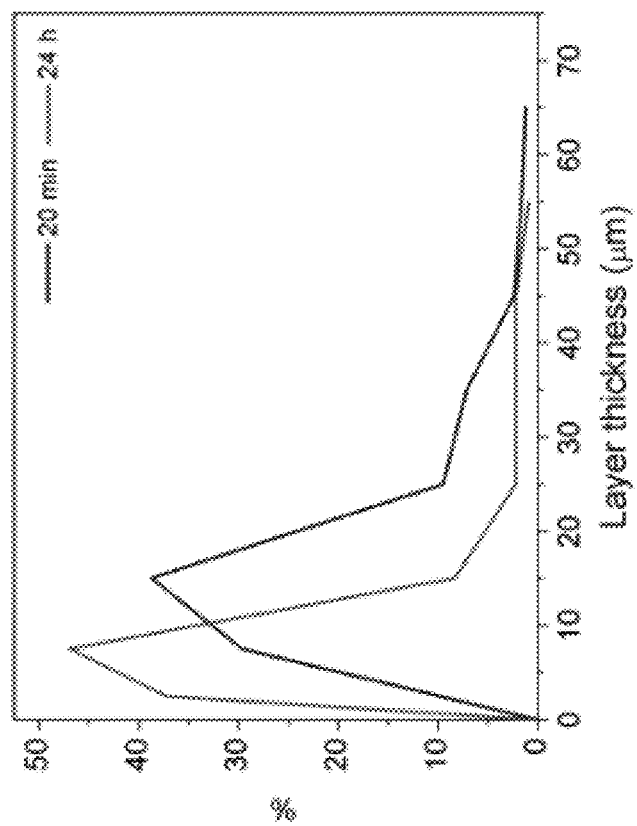
Figure 2B:
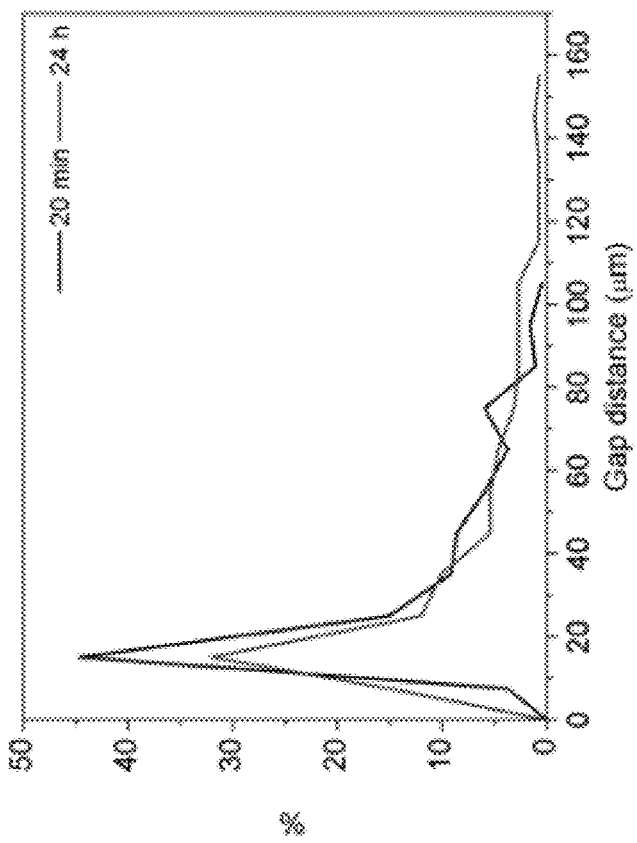

To maintain the integrity of nanofiber scaffolds following expansion, the scaffolds were freeze-dried using a lyophilizer. Nanofiber scaffolds were then cut along two different planes (x-y, y-z) and examined via scanning electron microscopy (SEM) to reveal the detailed fiber architecture of scaffolds. Prior to expansion, aligned electrospun PCL nanofiber mats were composed of densely packed fibrillar structures (FIG. 2A). In contrast, nanofiber scaffolds expanded for 20 minutes and 24 hours displayed layered structures with preserved nanotopographic cues rendered by aligned nanofibers (FIG. 2A). Gap distances were noted to increase with increasing reaction time (FIG. 2B). In contrast, layer thickness decreased from approximately 15 to 5 μm with increasing reaction time (FIG. 2C). Mechanical properties of aligned nanofiber scaffolds were also compared before and after expansion. Because of the layered architecture and high porosity of expanded nanofiber materials, the tensile modulus along both parallel and perpendicular to the direction of fiber alignment were lower compared to nanofiber mats before expansion (Table 1). The compressive Young's modulus of aligned nanofiber scaffolds, as measured along the x, y, and z directions was lower after expansion as compared to nanofiber mats before expansion (Table 1). Randomly oriented PCL nanofiber mats showed results similar to aligned nanofiber mats after treatment with an aqueous solution of $NaBH_4$ except that the degree of expansion was a little less for random mats compared to aligned mats (FIG. 3). The tensile modulus and Young's modulus were similarly reduced in randomly oriented nanofiber scaffolds following expansion (Table 2). The values of ultimate tensile stress, ultimate tensile strain, maximum stress, break stress and break strain along the x and y directions were missing in Tables 1 and 2 because all the samples were not broken along the x and y directions at the maximum tensile force (500 mN). The expansion resulted in layered structures of nanofiber scaffolds along the z direction. Because of the layered structures, the post-expansion scaffolds can be readily split between layers during the tensile strength test along the z direction. Therefore, the tensile properties of post-expansion scaffolds along the z direction were not presented in Table 1 and Table 2.

TABLE 1

Mechanical property of aligned PCL nanofiber scaffolds pre- and post-expansion. Ranges given for the nanofiber scaffolds include all experimental groups.

| | aligned PCL nanofiber scaffolds pre-expansion | | | aligned PCL nanofiber mat post-expansion | | |
|---|---|---|---|---|---|---|
| | X (parallel) | Y (vertical) | Z | X (parallel) | Y (vertical) | Z |
| Tensile Properties | | | | | | |
| ultimate tensile stress | N/A | 3679.5-211758.7 Pa | 876.0-1241.5 Pa | N/A | N/A | N/A |
| ultimate tensile strain | N/A | 57.4-66.9% | 33.5-51.8% | N/A | N/A | N/A |
| maximum stress | N/A | 5793.2-24049.6 Pa | 2611.7-4029.6 Pa | N/A | N/A | N/A |
| break stress | N/A | 2612.8-6388.9 Pa | 115.3-1319.6 Pa | N/A | N/A | N/A |
| break strain | N/A | 167.2-819.2% | 249.3-362.0% | N/A | N/A | N/A |
| tensile modulus | 18.6-38.2 kPa | 5.9-32.2 kPa | 1956.4-3812.9 Pa | 26.0-33.0 MPa | 454.5-719.5 kPa | N/A |
| Compressive Properties | | | | | | |
| Young's modulus (E) | 452.6-1743.0 Pa | 83.0-234.2 Pa | 450.6-584.7 Pa | 1064.5-4446.6 kPa | 911.5-1470.8 kPa | 1208.6-1590.0 kPa |

TABLE 2

Mechanical property of random PCL nanofiber scaffolds pre- and post-expansion. Ranges given for the random PCL nanofiber scaffolds include all experimental groups.

| | random PCL nanofiber scaffolds pre-expansion | | random PCL nanofiber scaffolds post-expansion | |
|---|---|---|---|---|
| | X, Y | Z | X, Y | Z |
| Tensile Properties | | | | |
| ultimate tensile stress | N/A | 179.9-1120.8 Pa | N/A | N/A |
| ultimate tensile strain | N/A | 43.1-70.7% | N/A | N/A |
| maximum stress | N/A | 179.9-1120.8 Pa | N/A | N/A |
| break stress | N/A | 1.4-48.8 Pa | N/A | N/A |
| break strain | N/A | 190.3-422.8% | N/A | N/A |
| tensile modulus | 125.5-265.8 kPa | 251.3-482.0 Pa | 1090.5-4114.5 kPa | N/A |
| Compressive Properties | | | | |
| Young's modulus (E) | 377.5-817.7 Pa | 240.9-323.8 Pa | 204.6-570.0 kPa | 885.1-1093.2 kPa |

Figures 4A, 4B:
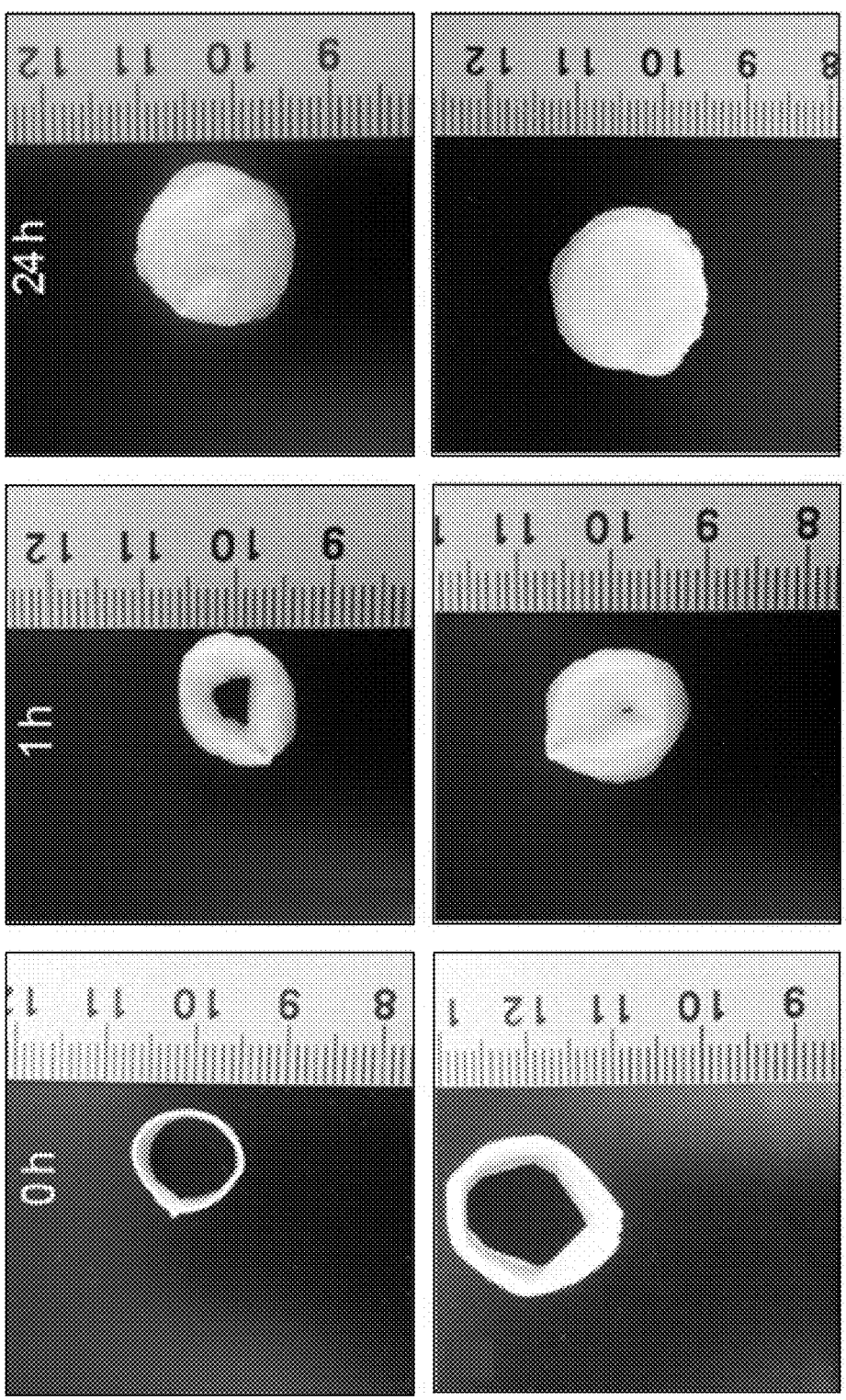
FIGS. 4A, 4B, 4C, and 4D show the expansion and characterization of tubular nanofiber scaffolds.
Figure 4C:
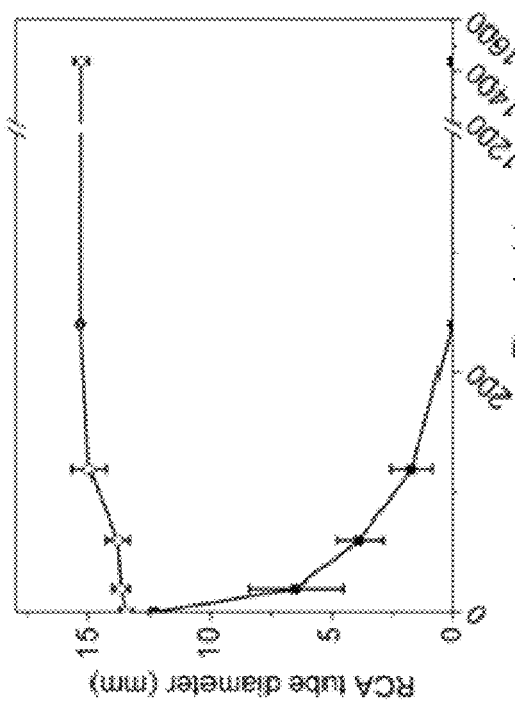
Figure 4D:
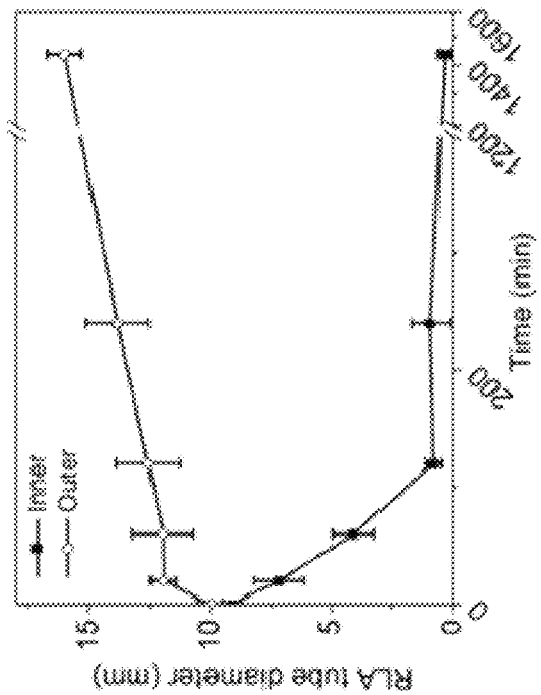
Figure 5:
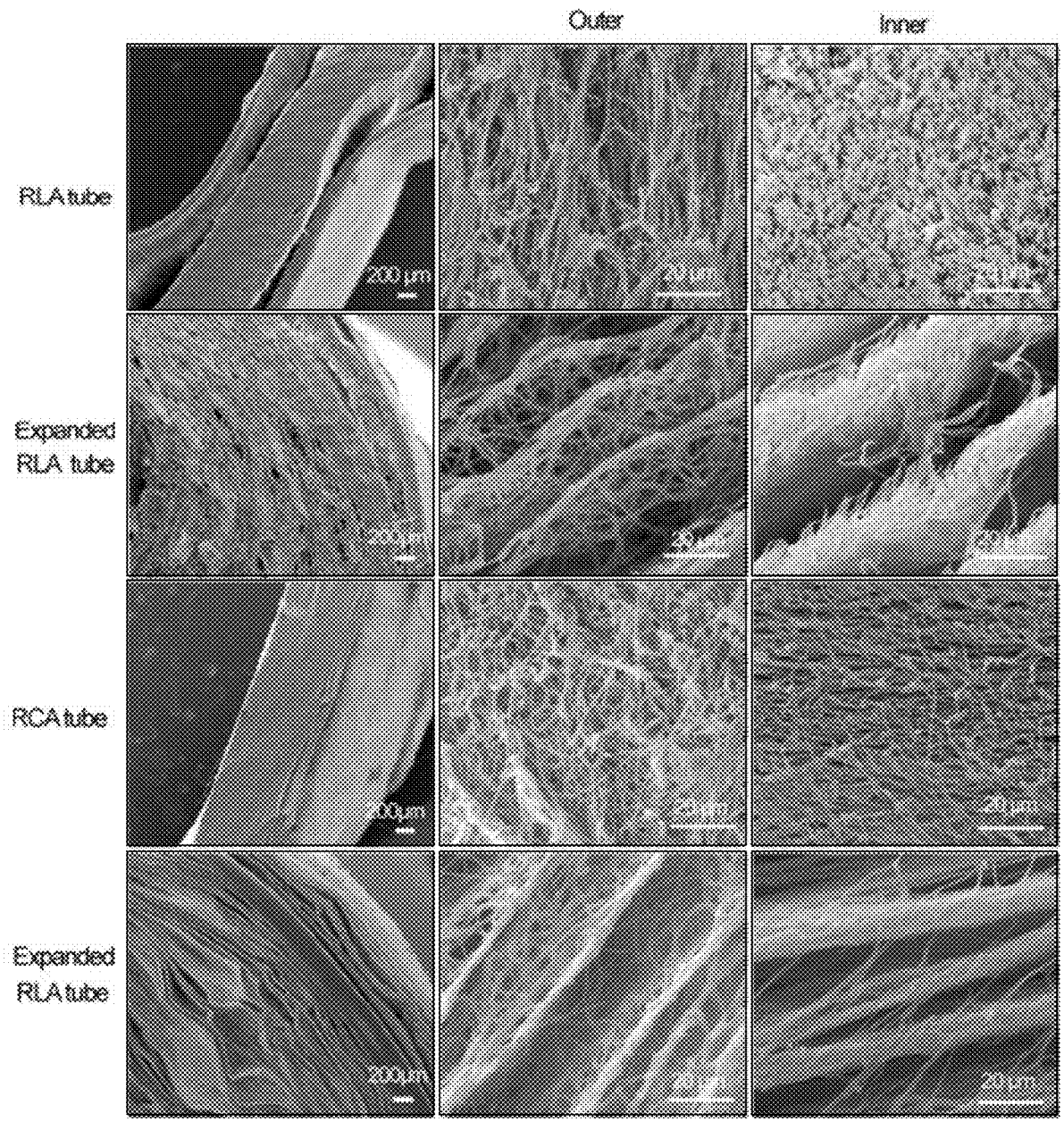
FIG. 5 shows the morphology of tubular nanofiber scaffolds. SEM images showing cross-section morphologies of tubular nanofiber scaffolds (RLA and RCA) before and after expanding in 1 M solution of $NaBH_4$ for 24 hours. Tubular nanofiber scaffolds formed layered structures after expansion.

The present method of expansion was applied to nonplanar nanofiber scaffolds in order to form tubular scaffolds ideal for regeneration of organized tissues such as nerve, blood vessel, and tendon (Panseri et al. (2008) BMC Biotechnol., 8:39; Hashi et al. (2007) Proc. Natl. Acad. Sci., 104:11915-11920; Hogan et al. (2011) J. Am. Acad. Orthop. Surg., 19:134-142). Successful fabrication of bilayer nanofiber conduits consisting of an outer layer of randomly oriented electrospun nanofibers and an inner layer of longitudinally aligned electrospun nanofibers has been demonstrated (Xie et al. (2014) ACS Appl. Mater. Interfaces 6:9472-9480; Xie et al. (2010) Nanoscale 2:35-44). Despite a unique multilumen design, fabricated conduits did not contain scaffold materials within the inner lumen of the conduit. Additional studies attempted to deliver longitudinally aligned nanofiber thin films within the inner lumen of nanofiber conduits in order to enhance nerve regeneration (Clements et al. (2009) Biomaterials 30:3834-3846; Mukhatyar et al. (2014) Ann. Biomed. Eng., 42:1436-1455). Sequential deposition of random and aligned nanofibers, following manual wrapping around a tubular mandrel, generated dual-layer nanofiber conduits consisting of an outer layer of randomly oriented nanofibers and an inner layer of longitudinally aligned nanofibers (FIG. 4A). Treatment of dual-layered nanofiber conduits with an aqueous solution of 1 M $NaBH_4$ was observed to expand the nanofiber material and fill the entire lumen of the tubes (FIG. 4A). Similar results were observed for dual-layer nanofiber conduits composed of an outer layer of randomly oriented nanofibers and an inner layer of circumferentially aligned nanofibers (FIG. 4B). The inner and outer diameters of nanofiber tubes were also during the expansion in aqueous media. After 24 hours of treatment with an aqueous solution of 1 M $NaBH_4$, the inner diameter of the dual-layer conduit, consisting of an outer layer of randomly oriented nanofibers and an inner layer of longitudinally aligned nanofibers, approached zero with expanded fibers occupying the entire lumen of the tubes (FIG. 4C). In contrast, the inner diameter of dual-layer nanofiber tubes composed of an outer layer of randomly oriented nanofibers and an inner layer of circumferentially aligned nanofibers approached zero after only 4 hour treatment with 1 M $NaBH_4$ solution (FIG. 4D). Similar to planar nanofiber materials, expanded tubular scaffolds formed layered nanofiber architectures oriented in concentric, circumferential layers extending the length of the construct (FIG. 5). Importantly, tubular nanofiber scaffolds maintained anisotropic properties in the inner layer of nanofibers (Figures). The maintenance of fiber alignment post-expansion is important in a variety of regenerative medical applications in which topographic cues are the key to organize regenerating cell populations and tissues. Specifically, expanded constructs consisting of aligned fibers are ideally suited to provide contact guidance cues necessary for enhancing and directing cell migration and axonal outgrowth during nerve repair/regeneration (Bellamkonda, R. V. (2006) Biomaterials 27:3515-3518; Patel et al. (2007) Nano Lett., 7:2122-2128).

Figure 6A:
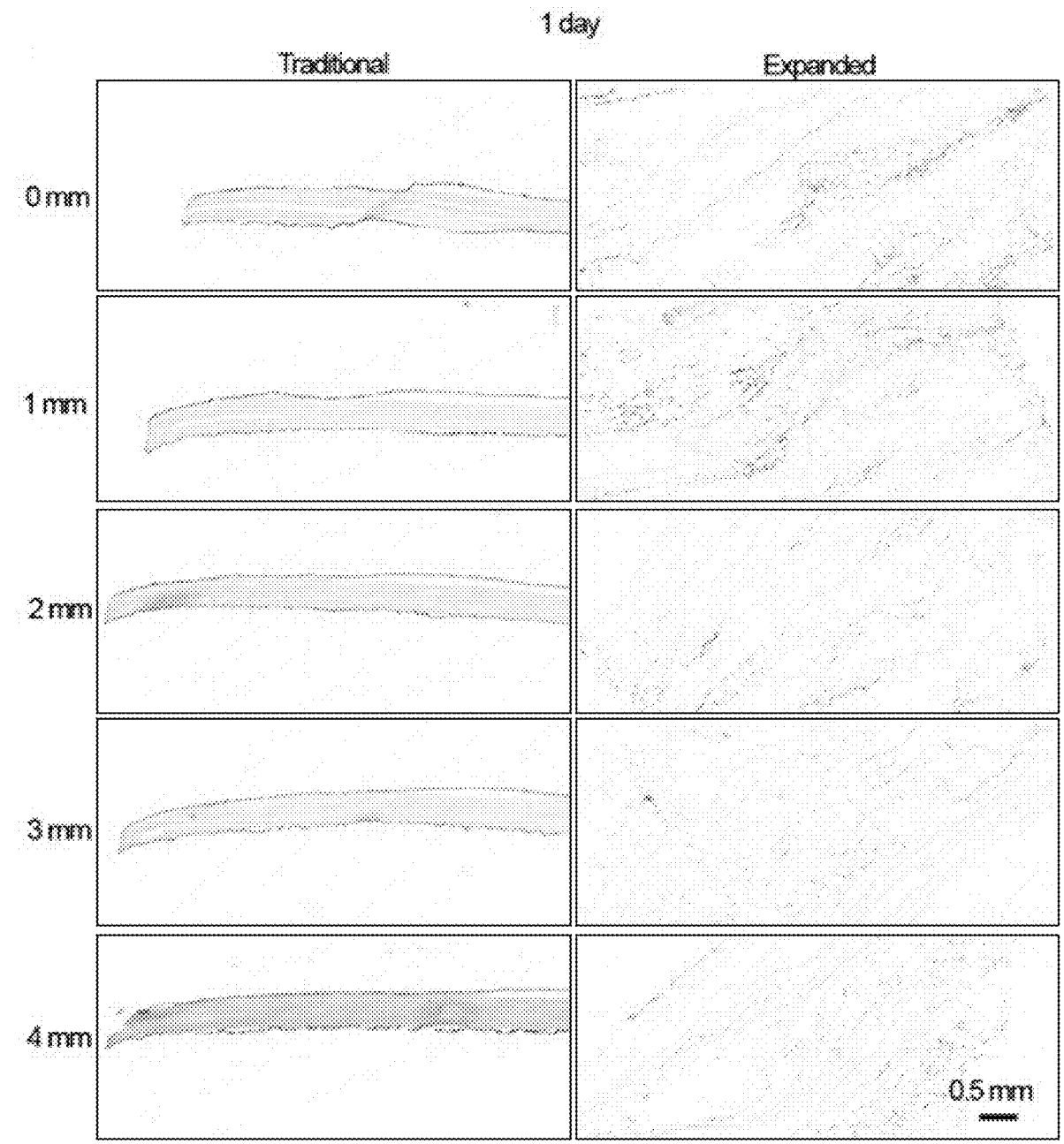
FIGS. 6A and 6B show hematoxylin-eosin staining of aligned PCL nanofiber scaffolds (unexpanded vs. expanded) with NIH3T3 fibroblasts seeding after incubation for 1 day (FIG. 6A) and 7 days (FIG. 6B). The scaffolds were sectioned at a thickness of 1 mm for hematoxylin-eosin staining. Cells were distributed on the surface of traditional nanofiber scaffolds. In contrast, cells were distributed throughout the whole expanded scaffolds.
Figure 6B:
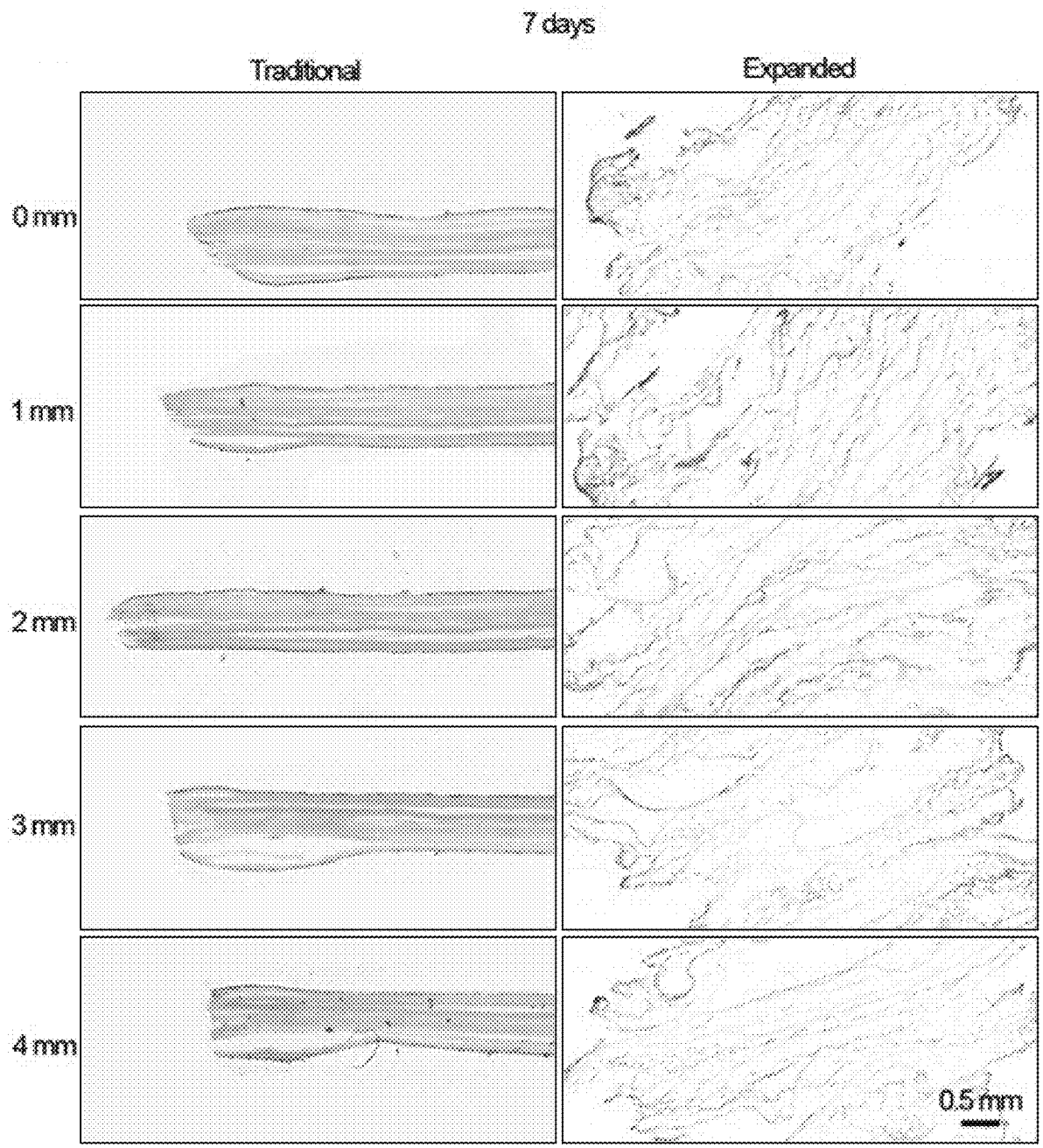
Figure 7A:
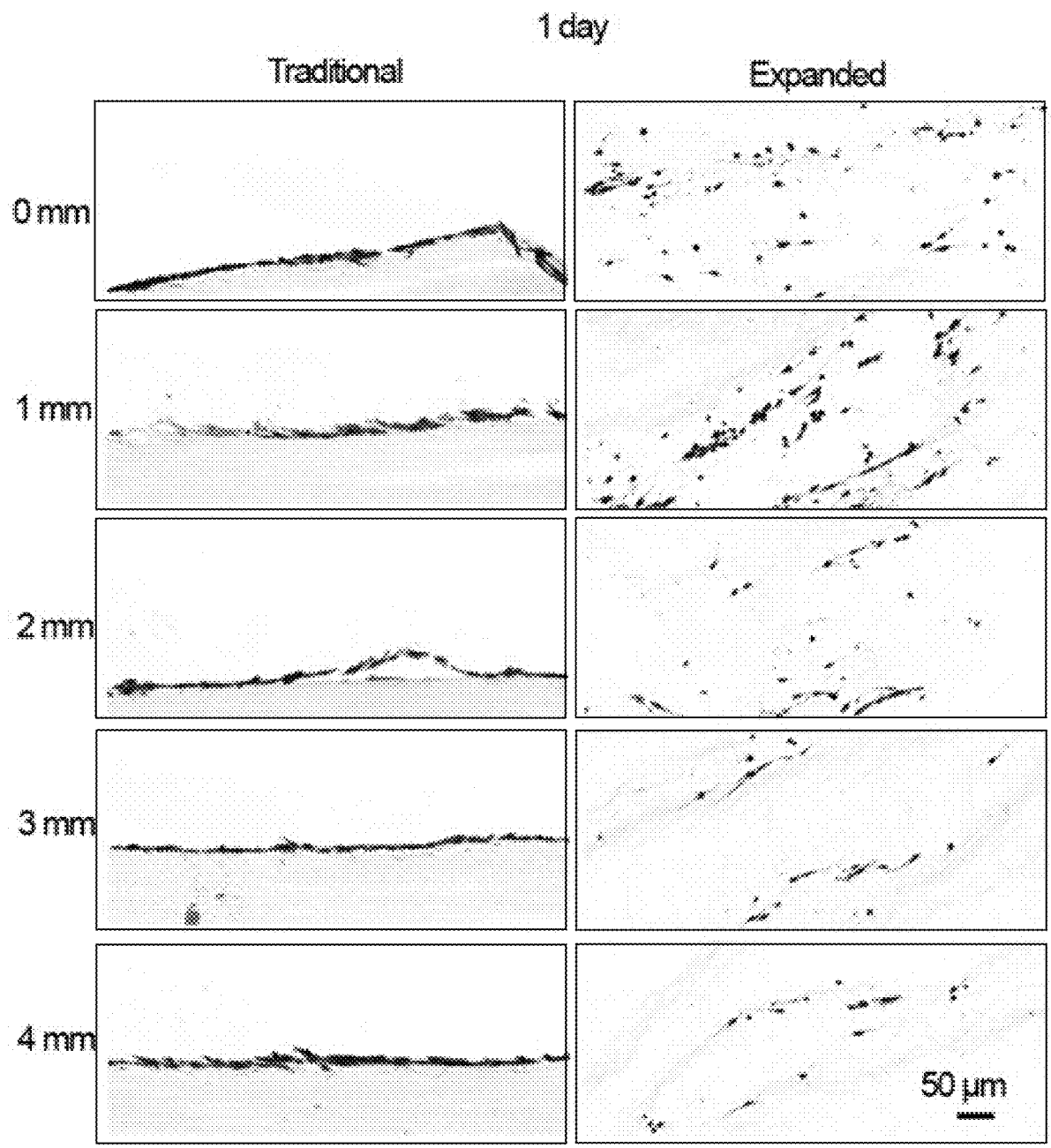
FIGS. 7A and 7B show highly magnified images of FIGS. 6A and 6B. Hematoxylin-eosin staining of aligned PCL nanofiber scaffolds (unexpanded vs. expanded) with NIH3T3 fibroblasts seeding after incubation for 1 day (FIG. 7A) and 7 days (FIG. 7B). The scaffolds were sectioned at a thickness of 1 mm for hematoxylin-eosin staining. Cells were distributed on the surface of traditional nanofiber scaffolds. In contrast, cells were distributed throughout the whole expanded scaffolds.
Figure 7B:
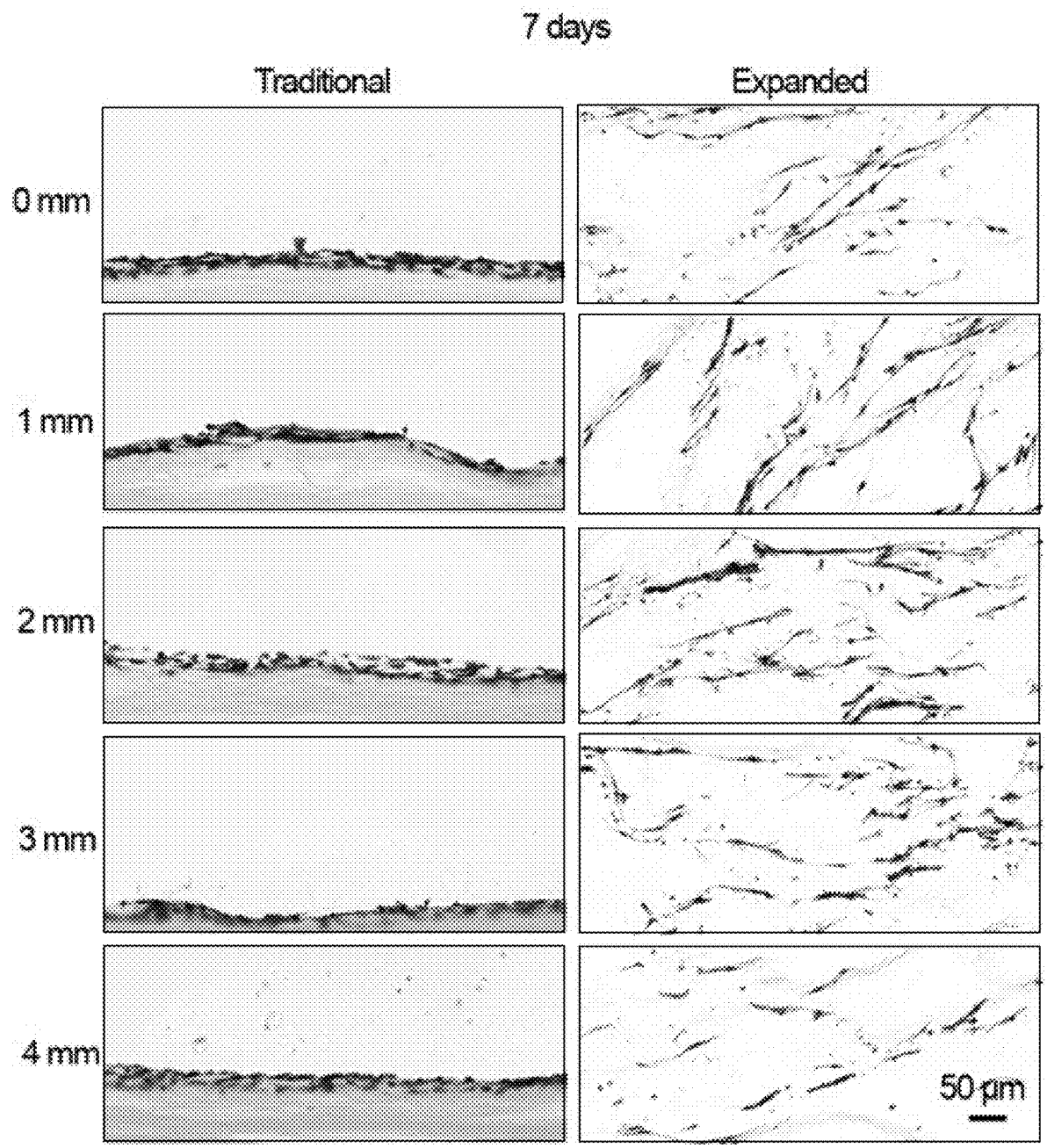

To generate a 3D tissue construct, the scaffold itself plays an important role as it provides not only a biomimetic architecture but also a substrate supporting cellular adhesion and growth along with certain cues to regulate cellular behaviors (Murphy et al. (2014) Nat. Mater., 13:547-557). In the present study, NIH3T3 fibroblasts were seeded to planar electrospun scaffolds consisting of aligned nanofibers before (1 mm thick) and after (1 cm thick) expansion, and incubated them for 1 day and 7 days. Fibroblasts were chosen as a model cell for cell culture in order to show cell infiltration and distribution after seeding and proliferating. In addition, fibroblasts are related to tendon and ligament tissue regeneration. Hematoxylin-eosin (H&E) staining of cell-seeded scaffolds indicated that cells successfully infiltrated and proliferated throughout the bulk of expanded nanofiber scaffolds (FIG. 6). In comparison, cells did not penetrate the unexpanded nanofiber scaffolds and only proliferated on the surface of the material (FIG. 7). Even after 7 days of culture, only several cell layers were observed on the surface of unexpanded nanofiber scaffolds and no cellular infiltration was noted within the bulk of the scaffolds (FIG. 7). Importantly, cellular morphology was consistent between expanded and unexpanded scaffolds, as cells displayed an elongated shape along the direction of fiber alignment. This observation indicates that expanded scaffolds maintained the topographic cues rendered by aligned nanofibers.

Figure 9:
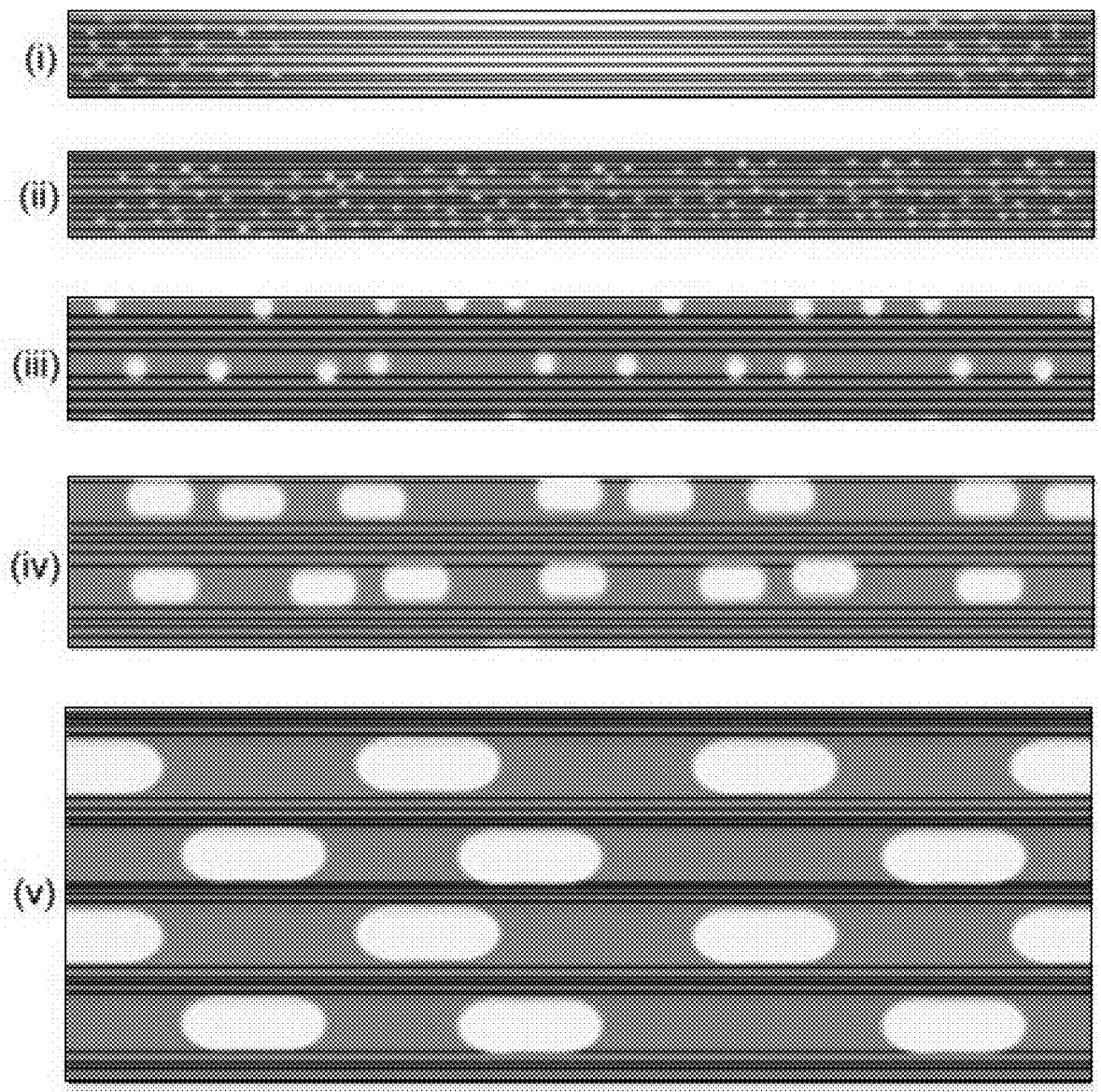
FIG. 9 provides a schematic illustrating the expanding process of nanofiber scaffolds in the $NaBH_4$ solution: (i) rapid penetration of the $NaBH_4$ aqueous solution into the aligned nanofiber scaffolds rapidly as driven by capillary effect; (ii) heterogeneous nucleation of gas bubbles on the surface of nanofibers or at intersections of imperfectly aligned nanofibers; (iii) growth of the nucleated bubbles upon the continued production of more and more hydrogen; (iv) coalescence of adjacent gas bubbles; and (v) formation of a "bubble layer" because of the further growth and coalescence of gas bubbles.

It has been shown herein that hydrogen gas bubbles generated from the $NaBH_4$ hydrolysis reaction expanded aligned electrospun nanofiber mats in the third dimension, resulting in formation of layered architectures and simultaneously maintenance of imparted anisotropic cues. Gas bubble formation in the 1 M $NaBH_4$ solution was observed both with and without presence of electrospun nanofiber scaffolds (FIG. 8). On the basis of these observations and without being bound by theory, the expansion process is purported to occur via the following steps: (i) rapid penetration of the $NaBH_4$ aqueous solution into the aligned nanofiber scaffolds rapidly as driven by capillary effect; (ii) heterogeneous nucleation of gas bubbles on the surface of nanofibers or at intersections of imperfectly aligned nanofibers; (iii) growth of the nucleated bubbles upon the continued production of hydrogen gas; (iv) coalescence of adjacent gas bubbles; and (v) formation of a "bubble layer" secondary to further growth and coalescence of gas bubbles (FIG. 9).

During the expansion, bubbles were observed to escape from the surface of the nanofiber matrix into the solution and into the atmosphere. The expansion of random nanofiber scaffolds is anticipated to follow a similar process except that slower penetration of the aqueous solution into randomly oriented nanofiber scaffolds due to increased nanofiber entanglement may lead to the slower expansion rates (FIG. 3). Similarly, maximum expansion of randomly oriented nanofiber scaffolds may be reduced compared to that of aligned scaffolds because of a strong interaction between intertwined nanofibers.

Figure 10A:
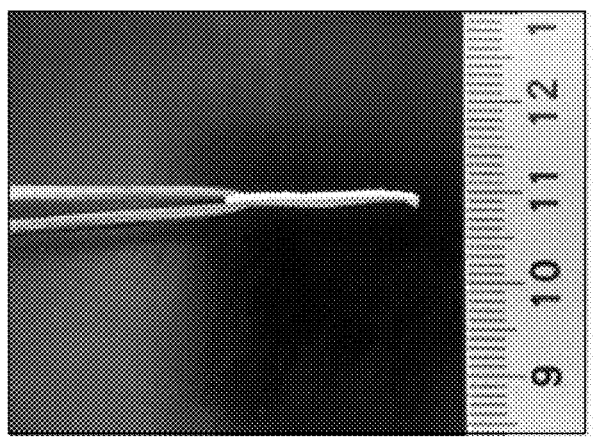
FIGS. 10A and 10B show the morphology of nanofiber scaffolds. Photographs showing aligned nanofiber scaffolds before (FIG. 10A) and after (FIG. 10B) expansion. The scaffold in FIG. 10B was dipped in 1 M $NaHCO_3$ and 1 M HCL solutions alternatively for several rounds.
Figure 10B:
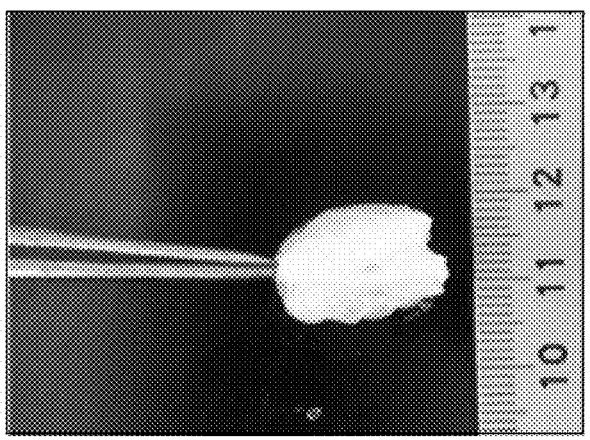
Figure 11:
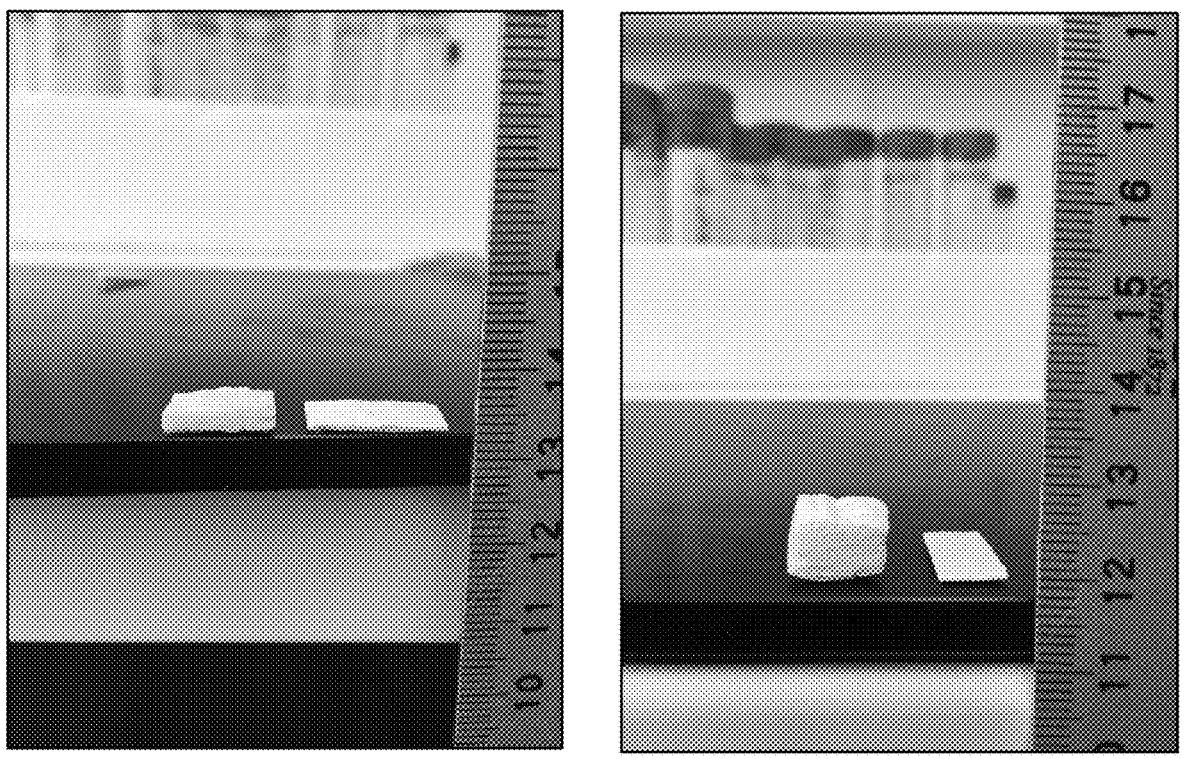
FIG. 11 provides two images of nanofiber membranes where the sample on the right in each image is before expansion and the sample on the left in each image is after expansion in liquid $CO_2$.

Though several studies have investigated means of fabricating 3D electrospun nanofiber scaffolds, few studies have focused on the fabrication of anisotropic scaffolds made of uniaxially aligned nanofibers (Blakeney et al. (2011) Biomaterials 32:1583-1590; Lee et al. (2011) Tissue Eng., Part A, 17:2695-2702; Cai et al. (2013) Langmuir 29:2311-2318; Sheikh et al. (2014) Nanomedicine 11:681-691; Jeong et al. (2014) J. Mater. Chem. B 2:8116-8122). The methods of the instant invention allow for expansion in both uniaxially aligned and randomly oriented nanofiber scaffolds in the third dimension using gas bubbles generated by $NaBH_4$ hydrolysis. Although the present study utilized an aqueous solution to focally initiate bubble generation within nanofiber mats, multiple methods of gas production may be successfully applied to achieve the same effect (e.g., dissolved gas, high-pressure gas liquid/fluid, and acoustic induction) (Leong et al. (2011) Acoust. Aust., 39:54-63). The expansion of PCL nanofiber mats was also achieved after dipping them into 1 M $NaHCO_3$ and 1 MHCL solutions alternatively for several rounds (FIG. 10). Further, nanofiber membranes were also expanded using bubbles generated by liquid $CO_2$ (FIG. 11).

Previous studies demonstrated that uniaxially aligned nanofibers can provide contact guidance for directing and enhancing cell migration, cell alignment, myotube formation, axonal outgrowth, and wound healing (Murphy et al. (2014) Nat. Mater., 13:547-557; Choi et al. (2008) Biomaterials 29:2899-2906; Huang et al. (2006) Nano Lett., 6:537-542; Xie et al. (2009) ACS Nano 3:1151-1159). Furthermore, aligned nanofibers have been demonstrated to provide an instructive microenvironment for regulation of stem cell differentiation (Yin et al. (2010) Biomaterials 31:2163-2175; Xie et al. (2009) Biomaterials 30:354-362; Ren et al. (2013) Acta Biomater., 9:7727-7736). Although successful, these studies were limited to use of 2D nanofiber mats.

Herein, macro-scale, 3D nanofiber scaffolds were successfully formed while maintaining the nanotopographic cues imparted by uniaxially aligned nanofibers critical for regeneration of organized tissues such as nerve, muscle, and tendon. Utilizing this approach, nanofiber materials of different orders/alignments may be sequentially deposited and expanded in order to recapitulate complex tissue architectures and anatomies such as the gastrointestinal tract structure or annulus fibrosus (Bitar et al. (2014) Gastroenterology 146:1614-1624; Nerurkar et al. (2009) Nat. Mater., 8:986-992). In addition, the present method allows for the formation of 3D, composite, or hybrid scaffolds by filling the space between fiber layers with a variety of hydrogels or biological matrices. The nanofibers may also be labeled or modified with additional signaling molecules, using either surface conjugation/coating or encapsulation, in order to further modulate cellular responses and encourage tissue regeneration (Wegst et al. (2015) Nat. Mater., 14:23-36). These novel features clearly distinguish the present method of expanding nanofiber membranes and the resulting 3D electrospun nanofiber scaffolds from prior reports.

In summary, a controllable method for expanding electrospun nanofiber mats/membranes in the third dimension while preserving imparted anisotropic features and cues has been provided. 3D scaffolds formed using this method support robust cellular infiltration and proliferation throughout bulk of the materials. The present technique may be used to synthesize scaffolds and constructs for applications in regenerative medicine and in engineering 3D tissue models for drug screening and biological study. This novel processing technique may also be applied to the fabrication of advanced nanofiber scaffolds for use in a variety of medical applications.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing a microfibrous structure with increased porosity and thickness, the method comprising exposing a microfiber structure to gas bubbles, thereby increasing the porosity and thickness of the microfiber structure,
wherein said microfiber structure comprises a plurality of microfibers, and
wherein said microfiber structure comprises electrospun microfibers.

2. The method of claim 1, wherein said gas bubbles are generated as a product of a chemical reaction.

3. The method of claim 2, wherein said chemical reaction is the hydrolysis of sodium borohydride.

4. The method of claim 2, wherein said exposure comprises immersing said microfiber structure in a liquid comprising the reagents for said chemical reaction.

5. The method of claim 1, wherein said microfiber structure comprises a plurality of uniaxially-aligned microfibers, random microfibers, and/or entangled microfibers.

6. The method of claim 1, further comprising preparing said microfiber structure comprising a plurality of microfibers prior to said exposure to bubbles.

7. The method of claim 1, wherein said microfibers comprise hydrophobic polymers.

8. The method of claim 7, wherein said hydrophobic polymer is poly(caprolactone).

9. The method of claim 1, wherein said method further comprises washing the produced microfibrous structure and removing gas bubbles trapped within said microfibrous structure.

10. The method of claim 1, wherein said method further comprises lyophilizing the produced microfibrous structure.

11. The method of claim 1, wherein said microfiber structure comprises biodegradable fibers.

12. The method of claim 1, wherein said microfiber structure consists of a plurality of microfibers, and wherein said microfibers consist of a polymer.

13. The method of claim 12, wherein said polymer is a hydrophobic polymer.

14. The method of claim 1, wherein said microfiber structure is a microfiber mat prior to said exposure to gas bubbles.

* * * * *